United States Patent
Glimsdale

(10) Patent No.: US 12,035,900 B2
(45) Date of Patent: Jul. 16, 2024

(54) DEVICES AND METHODS FOR OCCLUDING ABNORMAL OPENINGS IN A PATIENT'S VASCULATURE

(71) Applicant: St. Jude Medical, Cardiology Division, Inc., St. Paul, MN (US)

(72) Inventor: Mathias C. Glimsdale, St. Michael, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 644 days.

(21) Appl. No.: 17/160,996

(22) Filed: Jan. 28, 2021

(65) Prior Publication Data

US 2021/0145422 A1 May 20, 2021

Related U.S. Application Data

(62) Division of application No. 16/233,197, filed on Dec. 27, 2018, now Pat. No. 10,925,588, which is a
(Continued)

(51) Int. Cl.
*A61B 17/12* (2006.01)
*A61B 17/00* (2006.01)

(52) U.S. Cl.
CPC .... *A61B 17/0057* (2013.01); *A61B 17/12109* (2013.01); *A61B 17/12122* (2013.01);
(Continued)

(58) Field of Classification Search
CPC ..... A61B 17/00; A61B 17/12; A61B 17/0057; A61B 17/12122; A61B 17/12172;
(Continued)

(56) References Cited

U.S. PATENT DOCUMENTS

| 5,846,261 A | 12/1998 | Kotula et al. |
| 5,944,738 A | 8/1999 | Amplatz et al. |

(Continued)

FOREIGN PATENT DOCUMENTS

| CN | 1672644 A | 9/2005 |
| CN | 101049267 A | 10/2007 |

(Continued)

OTHER PUBLICATIONS

EP Search Report for EP Patent Application No. 19208926, mailed Dec. 20, 2019, 16 pages.
(Continued)

*Primary Examiner* — Vi X Nguyen
(74) *Attorney, Agent, or Firm* — Armstrong Teasdale LLP

(57) ABSTRACT

A medical device is provided in which one or both ends of the device encourage the formation of tissue across substantially the entire area of the respective end that is exposed to the blood flow for reducing the risk of a thrombotic embolism. The medical device includes a tubular structure having at least one expanded volume portion and a tapered transition portion. The tubular structure may be made through the braiding of a number of strands, and a first end feature may be used to secure the proximal strand ends. The proximal strand ends may be secured via the proximal end of the first end feature, such that the tapered transition portion is formed over the circumferential surface of the first end feature, and only a proximal end surface (or a portion of the proximal end surface) of the first end feature is exposed to the path of flowing blood.

17 Claims, 19 Drawing Sheets

Related U.S. Application Data division of application No. 14/243,271, filed on Apr. 2, 2014, now Pat. No. 10,201,337, which is a division of application No. 13/300,322, filed on Nov. 18, 2011, now Pat. No. 8,758,389.

(52) U.S. Cl.
CPC .. *A61B 17/12172* (2013.01); *A61B 17/12177* (2013.01); *A61B 2017/00526* (2013.01); *A61B 2017/00579* (2013.01); *A61B 2017/00592* (2013.01); *A61B 2017/00597* (2013.01); *A61B 2017/00606* (2013.01); *A61B 2017/00623* (2013.01); *A61B 2017/00867* (2013.01); *A61B 2017/12095* (2013.01)

(58) Field of Classification Search
CPC ........... A61B 2017/12095; A61B 2017/00867; A61B 2017/00637; A61B 2017/00654
See application file for complete search history.

(56) References Cited

U.S. PATENT DOCUMENTS

| | | | |
|---|---|---|---|
| 6,152,144 | A | 11/2000 | Lesh et al. |
| 6,168,622 | B1 | 1/2001 | Mazzocchi |
| 7,862,577 | B2 | 1/2011 | Gray et al. |
| 8,034,061 | B2 | 10/2011 | Amplatz et al. |
| 10,201,337 | B2 | 2/2019 | Glimsdale |
| 2001/0031981 | A1 | 10/2001 | Evans et al. |
| 2002/0068950 | A1 | 6/2002 | Corcoran et al. |
| 2002/0111648 | A1 | 8/2002 | Kusleika et al. |
| 2004/0153118 | A1 | 8/2004 | Clubb et al. |
| 2006/0241690 | A1 | 10/2006 | Amplatz et al. |
| 2007/0168019 | A1 | 7/2007 | Amplatz et al. |
| 2007/0233186 | A1 | 10/2007 | Meng |
| 2007/0265656 | A1 | 11/2007 | Amplatz et al. |
| 2008/0033475 | A1 | 2/2008 | Meng |
| 2009/0099647 | A1 | 4/2009 | Glimsdale et al. |
| 2009/0171386 | A1 | 7/2009 | Amplatz et al. |
| 2009/0209855 | A1* | 8/2009 | Drilling ........... A61B 17/12172 604/524 |
| 2009/0306706 | A1 | 12/2009 | Osypka |
| 2010/0023048 | A1 | 1/2010 | Mach |
| 2010/0121370 | A1* | 5/2010 | Kariniemi ........ A61B 17/12172 156/189 |
| 2011/0152993 | A1 | 6/2011 | Marchand et al. |
| 2012/0197283 | A1 | 8/2012 | Marchand et al. |

FOREIGN PATENT DOCUMENTS

| | | |
|---|---|---|
| CN | 200970282 Y | 11/2007 |
| CN | 101795628 A | 8/2010 |
| CN | 102149424 A | 8/2011 |
| CN | 102639181 A | 8/2012 |
| DE | 102006040415 B3 | 1/2008 |
| JP | 2007520271 A | 7/2007 |
| JP | 2008520359 A | 6/2008 |
| JP | 2011005292 A | 1/2011 |
| WO | 9912478 A1 | 3/1999 |
| WO | 03077799 A2 | 9/2003 |
| WO | 2008019590 A1 | 2/2008 |
| WO | 2011057002 A2 | 5/2011 |

OTHER PUBLICATIONS

International Search Report for Application No. PCT/US2012/064765, mailed Feb. 4, 2013, 7 pages.
Extended European Search Report for related EP Patent Application No. 23162995.7, mailed Jun. 5, 2023.

* cited by examiner

DEVICES AND METHODS FOR OCCLUDING ABNORMAL OPENINGS IN A PATIENT'S VASCULATURE

CROSS-REFERENCE TO RELATED APPLICATIONS

This application is a divisional application of U.S. patent application Ser. No. 16/233,197, filed Dec. 27, 2018, which is a divisional application of U.S. patent application Ser. No. 14/243,271, filed Apr. 2, 2014, now U.S. Pat. No. 10,201,337, which is a divisional application of U.S. patent application Ser. No. 13/300,322, now U.S. Pat. No. 8,758,389, filed on Nov. 18, 2011, which are hereby incorporated by reference in their entirety.

BACKGROUND

Field of the Invention

Embodiments of the present invention relate generally to medical devices for treating certain vascular abnormalities. In particular, embodiments are directed to medical devices and methods for occluding vascular abnormalities in which an end of the medical device is in the path of blood flow, such as closure of the Left Atrial Appendage (LAA), Atrial and Ventricular Septal Defects (ASD, VSD), and Patent Ductus Arteriosus (PDA) and the like.

Description of the Related Art

A wide variety of intravascular devices are used in various medical procedures. Certain intravascular devices, such as catheters and guidewires, are generally used simply to deliver fluids or other medical devices to specific locations within a patient's body, such as a selective site within the vascular system. Other, frequently more complex, devices are used in treating specific conditions, such as devices used in removing vascular occlusions or for treating septal defects and the like.

In certain circumstances, it may be necessary to occlude an abnormal opening in a patient's vessel, such as an abnormal opening between chambers of the heart, a channel, a hole, a cavity, or the like, so as to stop blood flow therethrough. For example, atrial fibrillation may result in the formation of a blood clot in the left atrial appendage (LAA), which may become dislodged and enter the blood stream. By occluding the LAA, the release of blood clots from the LAA may be significantly reduced, if not eliminated. Various techniques have been developed to occlude the LAA. For instance, balloon-like devices have been developed that are configured to be implanted completely within the cavity of the LAA, while surgical techniques have also been developed where the cavity of the LAA is inverted and surgically closed.

Despite these techniques, it would be advantageous to provide an improved occlusion device that offers an improved surface configuration to enhance tissue coverage or tissue in-growth, particularly on surfaces adjacent flowing blood, as well as increased flexibility, improved retention, improved thrombogenicity, and easier deployment and retrieval, thereby overcoming the shortcomings of conventional solutions for occluding abnormal openings within a patient's vasculature.

SUMMARY OF THE INVENTION

Embodiments therefore provide a medical device for occluding abnormal openings in a patient's vasculature. In general, the medical device is configured such that an end feature of the device is recessed within a tapered transition portion formed at a respective end of the medical device. In this way, only an end surface of the end feature (e.g., a proximal end surface of the end feature at the proximal end of the medical device), or a portion of this surface, is exposed to the flow of blood through the body lumen, and tissue in-growth over the end of the device may be enhanced and facilitated.

In one embodiment, a device is provided that is configured to self-expand from a contracted state when constrained within a delivery device toward an expanded state when deployed from the delivery device for delivery to a target site within the body lumen. The medical device may include a tubular structure and a first end feature. The tubular structure may comprise a plurality of braided strands, with each braided strand comprising a proximal strand end and a distal strand end. The first end feature may define a proximal end and a distal end, and the first end feature may be configured to receive and secure the proximal strand ends via the proximal end of the first end feature. The tubular structure may comprise an expanded volume portion proximate to the first end feature and a tapered transition portion extending between the expanded volume portion and the proximal end of the first end feature. In the expanded state, the expanded volume portion of the tubular structure may define an expanded volume diameter. Moreover, in the expanded state, the tapered transition portion may define a first transition diameter proximate the expanded volume portion and a second transition diameter proximate the proximal end of the first end feature. The first transition diameter may be greater than the second transition diameter, smaller than the expanded volume diameter, and disposed between the second transition diameter and the expanded volume diameter. In addition, the second transition diameter may be substantially equal to a diameter of the first end feature. In some cases, the second transition diameter may be sized to facilitate tissue growth over a proximal end of the medical device.

Embodiments of the medical device may also include a second end feature configured to receive and secure the distal strand ends of the plurality of braided strands. The medical device may define a central axis extending between the first end feature and the second end feature, and the expanded volume portion may define at least one surface that is substantially perpendicular to the central axis. In some cases, the expanded volume portion may define two surfaces that are substantially perpendicular to the central axis. The second end feature may define a proximal end and a distal end, and the second end feature may be configured to receive and secure the distal strand ends via the distal end of the second end feature.

In some cases, the expanded volume portion may be a first expanded volume portion and the tapered transition portion may be a first tapered transition portion. The tubular structure may further include a second expanded volume portion displaced from the first expanded volume portion and proximate the second end feature and a second tapered transition portion extending between the second expanded volume portion and the distal end of the second end feature. The expanded volume portion may be disk shaped.

The expanded volume portion may be a first expanded volume portion, and the tubular structure may further comprise a second expanded volume portion proximate the second end feature. The first expanded volume portion may be disk shaped, and the second expanded volume portion may be cylindrically shaped. The first expanded volume portion and the second expanded volume portion may be connected by a flexible connector such that the first and second expanded volume portions can articulate with respect to each other.

The second expanded volume portion may, in some cases, comprise a cone shaped end surface affixed to the connector. In addition, a plurality of hooks may be disposed on and may extend radially and axially outward from the second expansion volume portion. The hooks may be configured to engage body tissue when the device is moved along a central axis of the medical device in a proximal direction.

At least one of the first and second expanded volume portions may comprise a polymer fabric disposed therein, and at least a portion of the polymer fabric may extend substantially perpendicularly to the axis. The polymer fabric may be secured to a respective one of the first and second expanded volume portions.

In some embodiments, the medical device may define a proximal end and a distal end, and the proximal end of the first end feature may substantially coincide with the proximal end of the medical device. The medical device may be configured to occlude a vessel, cavity, hole, septal defect, or lumen in a body. For example, the medical device may be configured to occlude the left atrial appendage of the heart and to prevent thrombus from escaping therefrom.

In some cases, the tubular structure may be a first tubular structure, and the medical device may further comprise a second tubular structure comprising a second plurality of braided strands. The second plurality of braided strands may be comprised of a metal or polymer. The braided strands may comprise a metal having elastic properties, and/or the braided strands may comprise a shape memory alloy. The expanded volume portion may be heatset in a mold to memorize its expanded state.

The medical device may further comprise a polymer fabric disposed within the expanded volume portion, and the polymer fabric may be polyester.

In other embodiments, a medical device may be provided that is configured to self-expand from a contracted state when constrained within a delivery device toward an expanded state when deployed from the delivery device for delivery to a target site within the body lumen. The medical device may comprise a tubular structure and a first end feature. The tubular structure may comprise a plurality of braided strands, and each braided strand may comprise a proximal strand end and a distal strand end. The first end feature may have a proximal end and a distal end, and the first end feature may be configured to receive and secure the proximal strand ends via the proximal end of the first end feature. Moreover, the proximal end of the first end feature may comprise a proximal end surface, a distal end surface, and a circumferential surface extending between the proximal and distal end surfaces. The tubular structure may comprise an expanded volume portion proximate to the first end feature and a tapered transition portion extending between the expanded volume portion and the proximal end of the first end feature. In the expanded state, the proximal strand ends may be secured to the first end feature such that the transition portion substantially surrounds the circumferential surface of the first end feature and only the proximal end surface of the first end feature or a portion of the proximal end surface is exposed to fluid flow through the body lumen.

In still other embodiments, a medical device may be provided that is configured to self-expand from a contracted state when constrained within a delivery device toward an expanded state when deployed from the delivery device for delivery to a target site within the body lumen. The medical device may include a tubular structure comprising a plurality of braided strands, and each braided strand may comprise a proximal strand end and a distal strand end. The medical device may further include a first end feature having a proximal end and a distal end, where the first end feature is configured to receive and secure the proximal strand ends via the proximal end of the first end feature. The tubular structure may comprise an expanded volume portion proximate to the first end feature and a tapered transition portion extending between the expanded volume portion and the proximal end of the first end feature. In the expanded state, the proximal strand ends may be secured to the first end feature such that the proximal strand ends are at least partially inverted at the proximal end of the first end feature.

In still other embodiments, a method of making a medical device for placement in a body lumen is provided. The method includes braiding a plurality of strands defining proximal strand ends to form a tubular structure and attaching a first end feature defining a proximal end and a distal end to the proximal strand ends via the proximal end of the first end feature. The medical device may be configured to self-expand from a contracted state when constrained within a delivery device toward an expanded state when deployed from the delivery device for delivery to a target site within the body lumen. The tubular structure may comprise an expanded volume portion proximate to the first end feature and a tapered transition portion extending between the expanded volume portion and the proximal end of the first end feature. In the expanded state, the expanded volume portion of the tubular structure may define an expanded volume diameter. Furthermore, in the expanded state, the tapered transition portion may define a first transition diameter proximate the expanded volume portion and a second transition diameter proximate the proximal end of the first end feature. The first transition diameter may be greater than the second transition diameter, smaller than the expanded volume diameter, and disposed between the second transition diameter and the expanded volume diameter. The second transition diameter may be substantially equal to a diameter of the first end feature.

In still other embodiments, a method of delivering a medical device is provided. The method includes providing a medical device configured to self-expand from a contracted state when constrained within a delivery device toward an expanded state when deployed from the delivery device for delivery to a target site within the body lumen, where the medical device is configured as described above. The medical device may be advanced through a body lumen toward the target site and deployed at the target site.

BRIEF DESCRIPTION OF THE DRAWINGS

The foregoing features and advantages of embodiments of the invention will become apparent to those skilled in the art from the following detailed description of a preferred embodiment, especially when considered in conjunction with the accompanying drawings in which like numerals in the several views refer to corresponding parts.

DETAILED DESCRIPTION

Embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
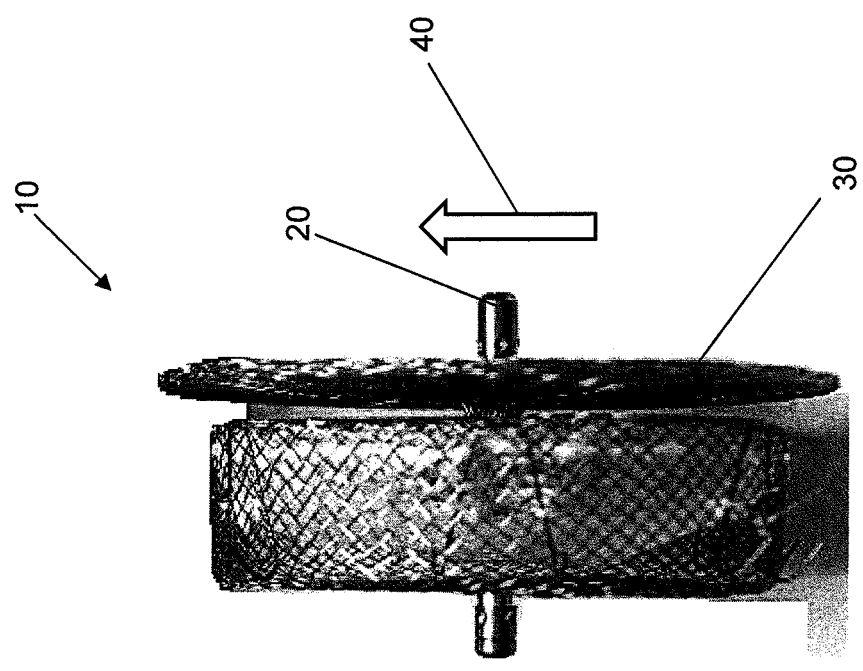
FIG. 1 illustrates a conventional medical device that includes protruding end clamps.

In general, embodiments of a medical device are described that provide an end feature that is recessed within a tapered transition portion formed at a respective end of the medical device, such that the end feature does not protrude from the respective end of the device. In this way, the medical device may be safely and easily deployed at target sites in certain locations of the patient's vasculature where blood flow may occur across one or both ends by providing a surface configuration that facilitates tissue coverage while reducing the risk of a thrombotic embolism. For example, in conventional devices, such as the device 10 shown in FIG. 1, an end clamp 20 may be provided at a proximal end of the medical device that protrudes outwardly from the braided structure 30. As a result, blood flow in the direction of the arrow 40 may be disrupted in the area of the end clamp 20. Because of the smooth surface of the clamp and its location in the stream of blood flow, tissue growth on the clamp may not occur as quickly as it occurs over other surfaces of the device. There is always a risk of clot formation over device surfaces prior to tissue incorporation, so anti-clotting medications may be prescribed to protect the patient during a period of time until tissue coverage is complete. Embolisms may form and dislodge from uncovered surfaces and may travel through the patient's vasculature, putting the patient at risk, so it is preferable to have device surfaces where tissue coverage is facilitated. Further examples of medical devices are provided in U.S. Publication No. US 2009/0171386 titled "Percutaneous Cather Directed Intravascular Occlusion Devices" and filed on Dec. 28, 2007, which is incorporated by reference herein in its entirety.

Figure 2:
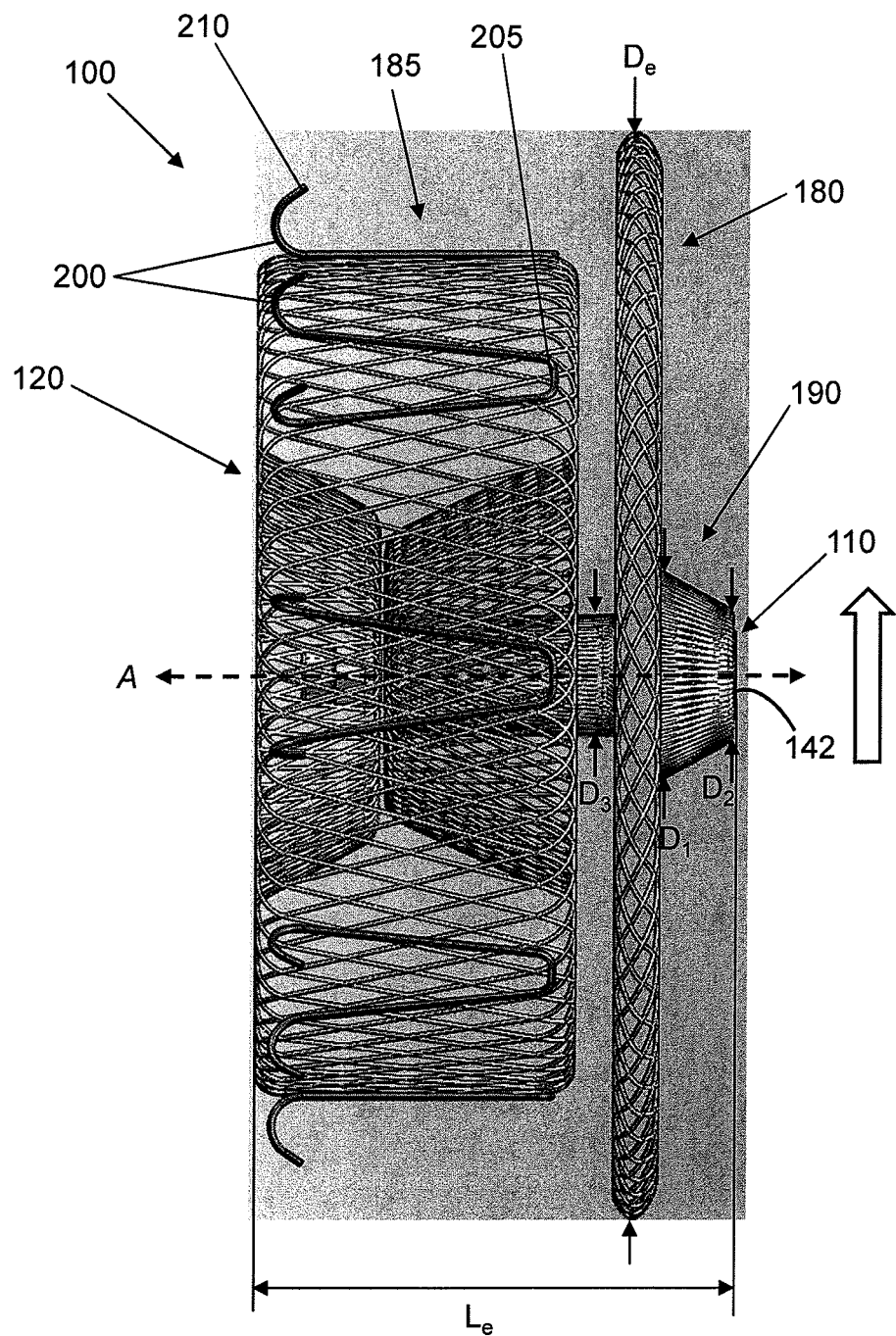
FIG. 2 is a schematic side view of a medical device in an expanded state according to an exemplary embodiment.

Accordingly, embodiments of the medical device 100, such as shown in FIG. 2, are configured such that one or both ends 110, 120 of the device encourage formation of tissue across substantially the entire area of the respective end that is exposed to the blood flow, such that the risk of a thrombotic embolism may be minimized. An illustration of a device that has been placed in the body lumen at a target site for a period of time, showing the growth of tissue 50 over at least the proximal end 110 of the device, is provided in FIG. 3. Moreover, embodiments of the present invention provide for attachment of the end feature(s) in such a way that radial expansion and contraction of the medical device as the medical device is moved between contracted and expanded states is facilitated as compared to conventional devices, as described in greater detail below.

It is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the medical device may be configured to bridge or otherwise support a variety of vascular abnormalities. For example, the vascular abnormality could be any abnormality that affects the shape of the native lumen, such as an LAA, an atrial septal defect, a lesion, a vessel dissection, or a tumor. Embodiments of the medical device may be useful, for example, for occluding an LAA, ASD, VSD, or PDA, as noted above. Furthermore, the term "lumen" is also not meant to be limiting, as the vascular abnormality may reside in a variety of locations within the vasculature, such as a vessel, an artery, a vein, a passageway, an organ, a cavity, or the like. For ease of explanation, the examples used herein refer to the occlusion of an LAA. As used herein, the term "proximal" refers to a part of the medical device or the delivery device that is closest to the operator, and the term "distal" refers to a part of the medical device or the delivery device that is farther from the operator at any given time as the medical device is being delivered through the delivery device.

According to one embodiment of the present invention for forming the medical device 100, a plurality of strands may be braided together to form a tubular structure. Although the strands are described as being braided, it is understood that according to additional embodiments of the present invention, the medical device 100 may be formed by braiding, interweaving, knitting, or otherwise combining filamentary materials together, such as by using a conventional braiding machine. These filamentary materials may include, for example, fibers, thread, yarn, cable, metallic wires, polymer monofilament or multifilament strands, and combinations of these materials, any of which are referenced herein as "strands," and such terms may be used interchangeably. The strands may be comprised of any material, such as natural materials, polymers, metals, metallic alloys, or combinations of the same. The strands may be braided to have a predetermined pick and pitch to define openings or fenestrations so as to vary the impedance of blood flow therethrough.

In some cases, other techniques may be used to form the tubular structure. For example, the tubular structure could be etched or laser cut from a tube such as to form an interstice geometry, or the tubular structure could comprise an occlusion material coupled to a scaffolding structure or a plurality of slices of a tubular member coupled together, such as via gluing. Moreover, it is understood that the medical device 100 may comprise one or more layers of occluding material such that the medical device may include a variety of occluding materials capable of at least partially inhibiting blood flow therethrough in order to facilitate the formation of thrombus.

Figure 4:
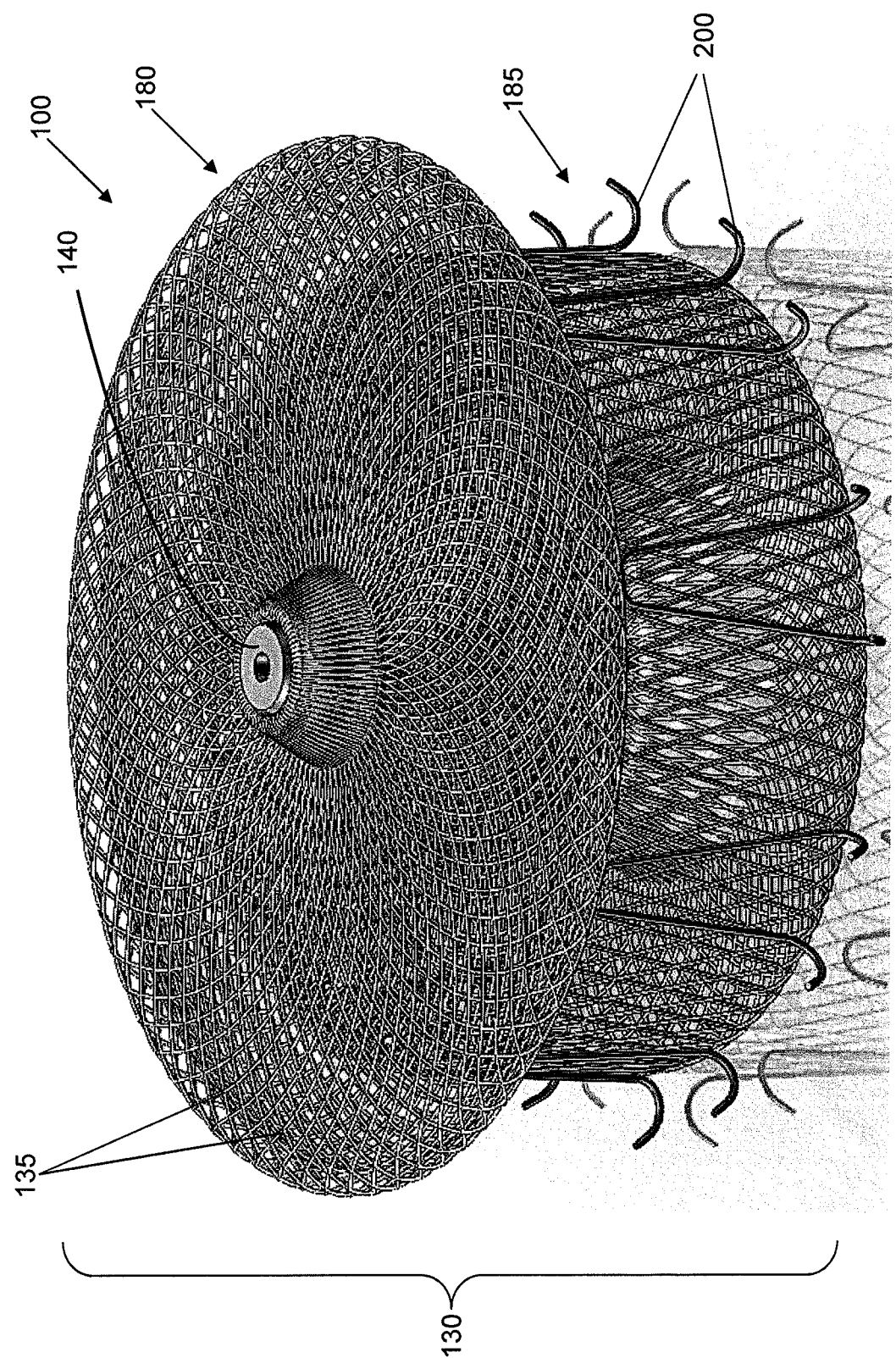
FIG. 4 is a schematic perspective view of the medical device of FIG. 2 in an expanded state from the proximal end according to an exemplary embodiment.

According to one embodiment, the occluding material of the tubular structure 130, shown in FIG. 4, is a metal fabric including a plurality of strands 135, such as two sets of essentially parallel generally helical strands, with the strands of one set having a "hand," or a direction of rotation, opposite that of the other set.

The pitch of the strands 135 (the angle defined between the turns of the strands and the axis of the braid) and the pick of the fabric (the number of wire strand crossovers per unit length) may be adjusted as desired for a particular application. The wire strands of the metal fabric used in one embodiment of the present method may be formed of a material that is both resilient and can be heat treated to substantially set a desired shape. Materials which may be suitable for this purpose include a cobalt-based low thermal expansion alloy referred to in the field as Elgiloy, nickel-based high temperature high-strength "superalloys" commercially available from Haynes International under the trade name Hastelloy, nickel-based heat treatable alloys sold under the name Incoloy by International Nickel, and a number of different grades of stainless steel. An important consideration in choosing a suitable material for the wires strands is that the wires retain a suitable amount of the deformation induced by the molding surface (as described below) when subjected to a predetermined heat treatment and elastically return to said molded shape after substantial deformation.

One class of materials which meets these qualifications is so-called shape memory alloys. One particular shape memory alloy that may be used is Nitinol. Nitinol alloys are also highly elastic and are said to be "superelastic," or "pseudoelastic." This elasticity may allow the device to return to a preset expanded configuration for deployment following passage in a distorted form through a delivery catheter. Moreover, other suitable materials include those that are compatible with magnetic resonance imaging (MRI), as some materials may cause heat or torque resulting from performing Mill, and some materials may distort the Mill image. Thus, metallic and/or non-metallic materials that reduce or eliminate these potential problems resulting from using Mill may be employed. Further examples of materials and manufacturing methods for medical devices with shape memory properties are provided in U.S. Publication No. 2007/0265656 titled "Multi-layer Braided Structures for Occluding Vascular Defects" and filed on Jun. 21, 2007, which is incorporated by reference herein in its entirety.

In some embodiments, one or more layers of fabric may be employed to form a medical device, as described in greater detail below. For example, two layers of metal fabric could be separately woven into tubular structures, with one tubular structure coaxially disposed within the second tubular structure. For further discussion regarding a multi-layer braided device and techniques for fabricating such a device, see U.S. Patent Appl. Publ. No. 2007/0168019 to Amplatz et al., which is hereby incorporated in its entirety by reference.

The tubular structure 130 used to fabricate medical devices 100 according to one embodiment of the present invention may use wire strands ranging in diameter from 0.0015 in. to 0.005 in., preferably in the range of 0.003 to 0.0045 in. The number of wires in the tubular braid may vary from 36 to 144 but preferably is in the range of 72 to 144. The pick count of the braid may vary from 30 to 100. The fabric may thus have an average area between supporting fibers of between approximately 0.0016 sq. cm. and 0.25 sq. cm.

Once an appropriately sized tubular structure is obtained, the fabric may be deformed to generally conform to a surface of a molding element. For example, the tubular structure 130 may be deformed to define one or more expanded volume portions 180, 185, as shown in FIG. 4. Deforming the fabric will reorient the relative positions of the wire strands of the metal fabric from their initial order to a second, reoriented configuration. The shape of the molding element should be selected to deform the fabric into substantially the shape of the desired medical device when unconstrained. Once the molding element is assembled with the metal fabric generally conforming to a molding surface of that element, the fabric can be subjected to a heat treatment while it remains in contact with that molding surface. After the heat treatment, the fabric may be removed from contact with the molding element and should substantially retain its shape in a deformed state.

Figure 5:
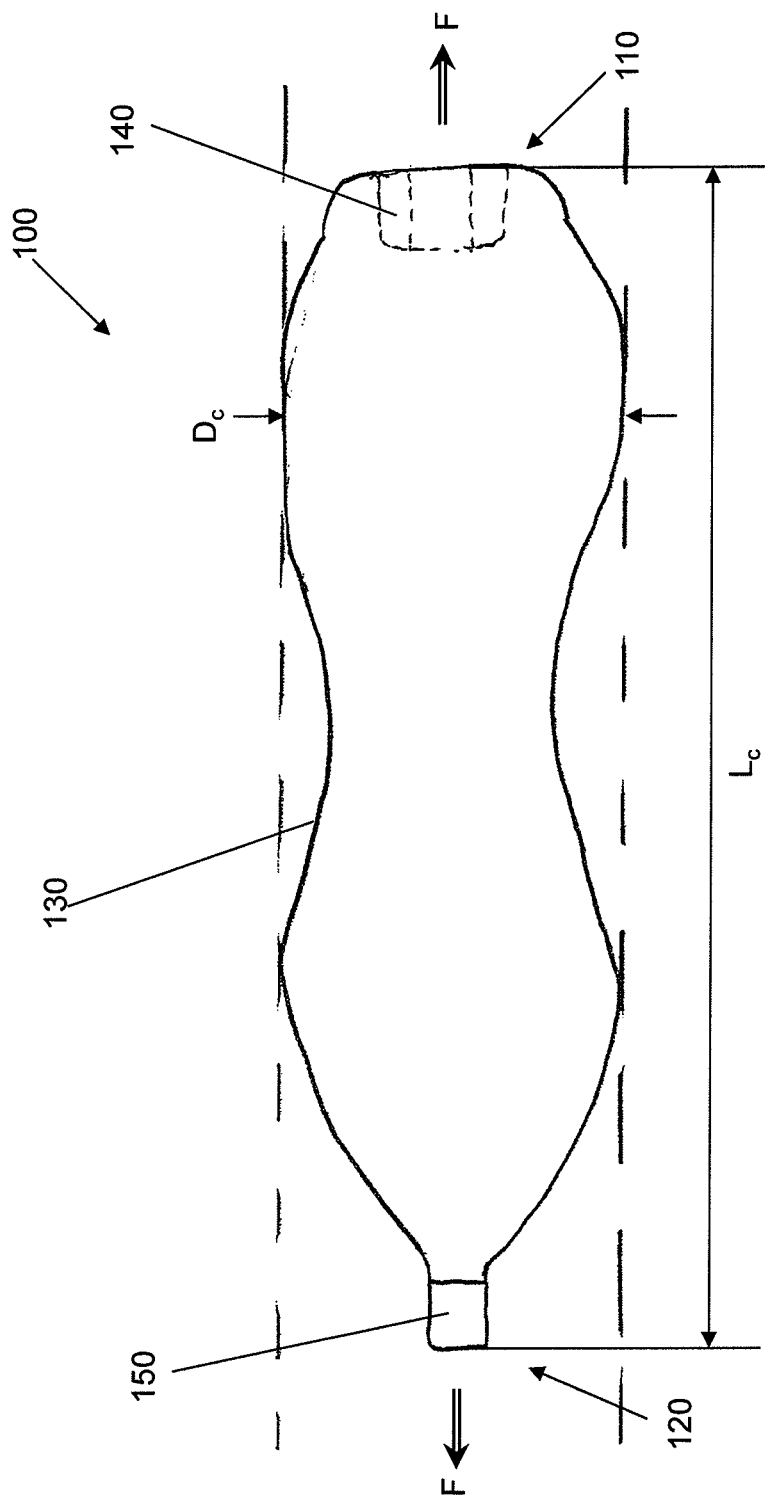
FIG. 5 is a schematic side view of the medical device of FIG. 2 in a contracted state according to an exemplary embodiment.

In this way, a medical device 100 may be formed that is configured to self-expand from a contracted state when constrained within a delivery device (such as a catheter, represented by dashed lines in FIG. 5) toward an expanded state when deployed from the delivery device for delivery to a target site within the body lumen (shown in FIG. 2). In the contracted state, the medical device 100 may define a length $L_c$, and in the expanded state the medical device may define a length $L_e$. The medical device 100 may be moved to the contracted state, for example, when the ends 110, 120 of the device are pulled away from each other and/or a radial constraint is applied to the device. In other words, as shown in FIG. 5, the application of a tensile force F on the ends of the device 100 may serve to collapse the overall outer diameter $D_e$ of the device such that it may achieve a reduced diameter $D_c$, allowing the device to be received within a lumen of a delivery device in the contracted state (FIG. 5) for delivery to the target site. Thus, in this example, the delivery device (e.g., a catheter) applies the radial constraint to maintain the medical device 100 in the contracted state.

The medical device 100 may be configured, however, such that, when the radial constraint is removed, the device can self-expand to the expanded state shown in FIG. 2. For example, as the medical device 100 is unsheathed from the delivery device, portions of the medical device that are no longer constrained by the delivery device may self-expand and freely return to the expanded state, and once the medical device has been fully deployed from the delivery device proximate the target site, the medical device will at least partially assume the expanded state. For example, the vessel diameter or the diameter of the opening in which the medical device 100 is inserted may limit complete return to the expanded state.

Thus, a medical device having a predetermined shape may be collapsed by longitudinally stretching the medical device (as illustrated in FIG. 5) for inserting the device into the lumen of a delivery device (e.g., a guide catheter or delivery sheath). The delivery device may then be positioned and advanced in a patient's body such that the distal end of the delivery device is adjacent to the target site (e.g., straddling the abnormal opening). The medical device 100 may be advanced through the delivery device such that the distal end of the medical device is near the distal end of the delivery device. Thus, as the medical device is deployed from the distal end of the delivery device, the diameter of the medical device is allowed to self-expand at the target site, e.g., to occlude the abnormal opening in the patient's vasculature.

Figure 6:
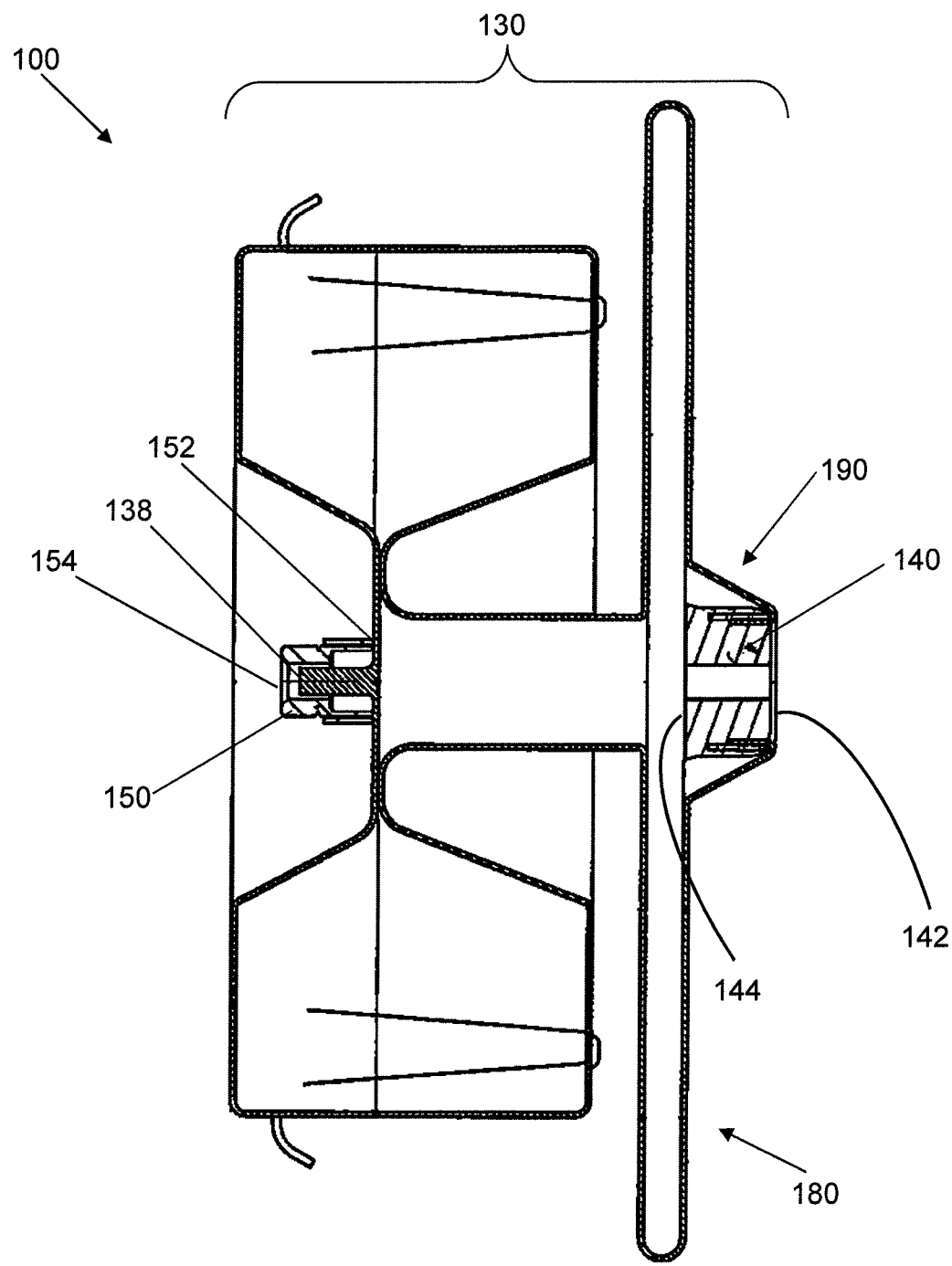
FIG. 6 is a simplified cross-sectional view of the medical device of FIG. 2 according to an exemplary embodiment.
Figure 7:
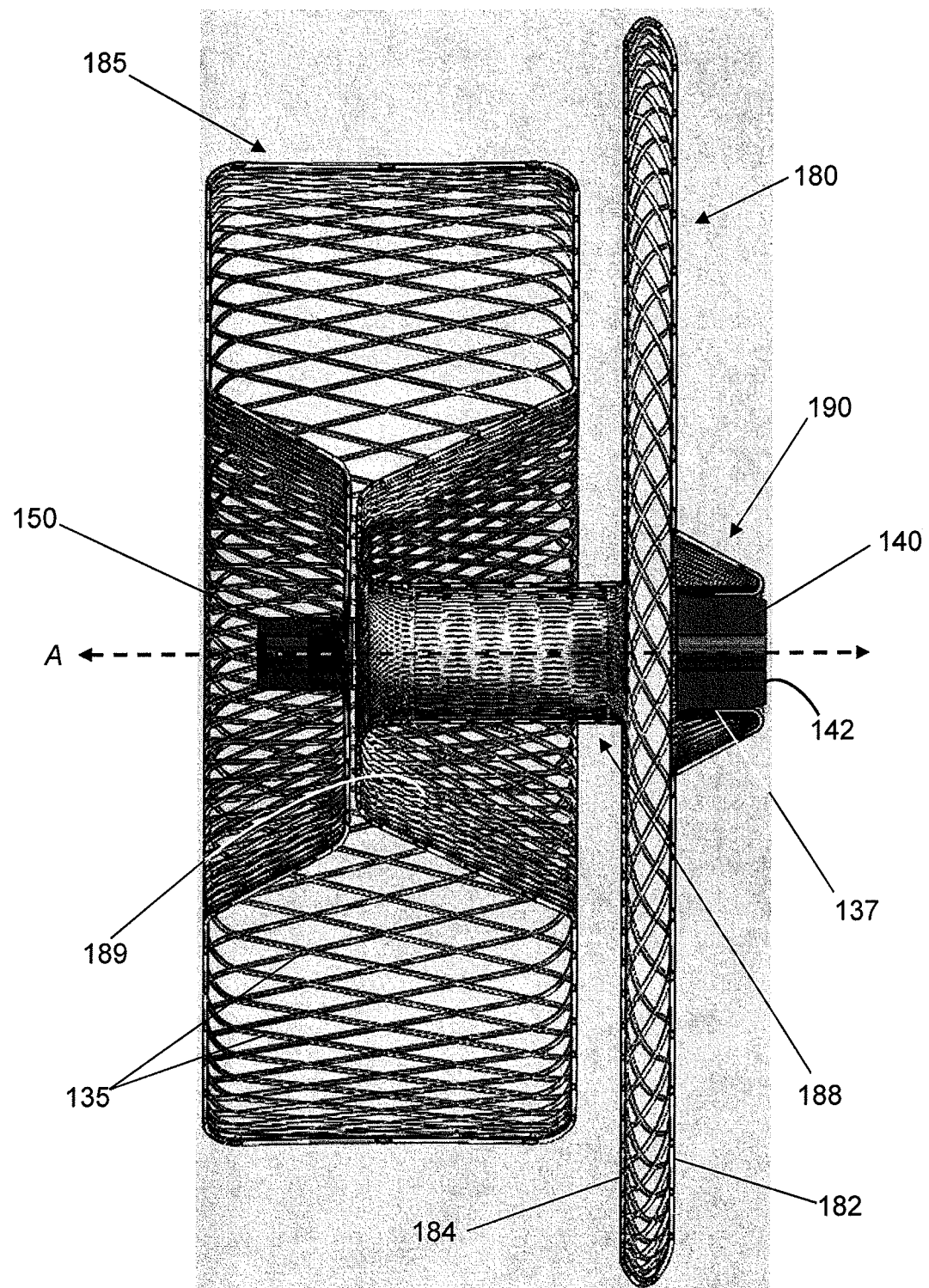
FIG. 7 is a cross-sectional view of the medical device of FIG. 2 according to an exemplary embodiment.
Figure 8:
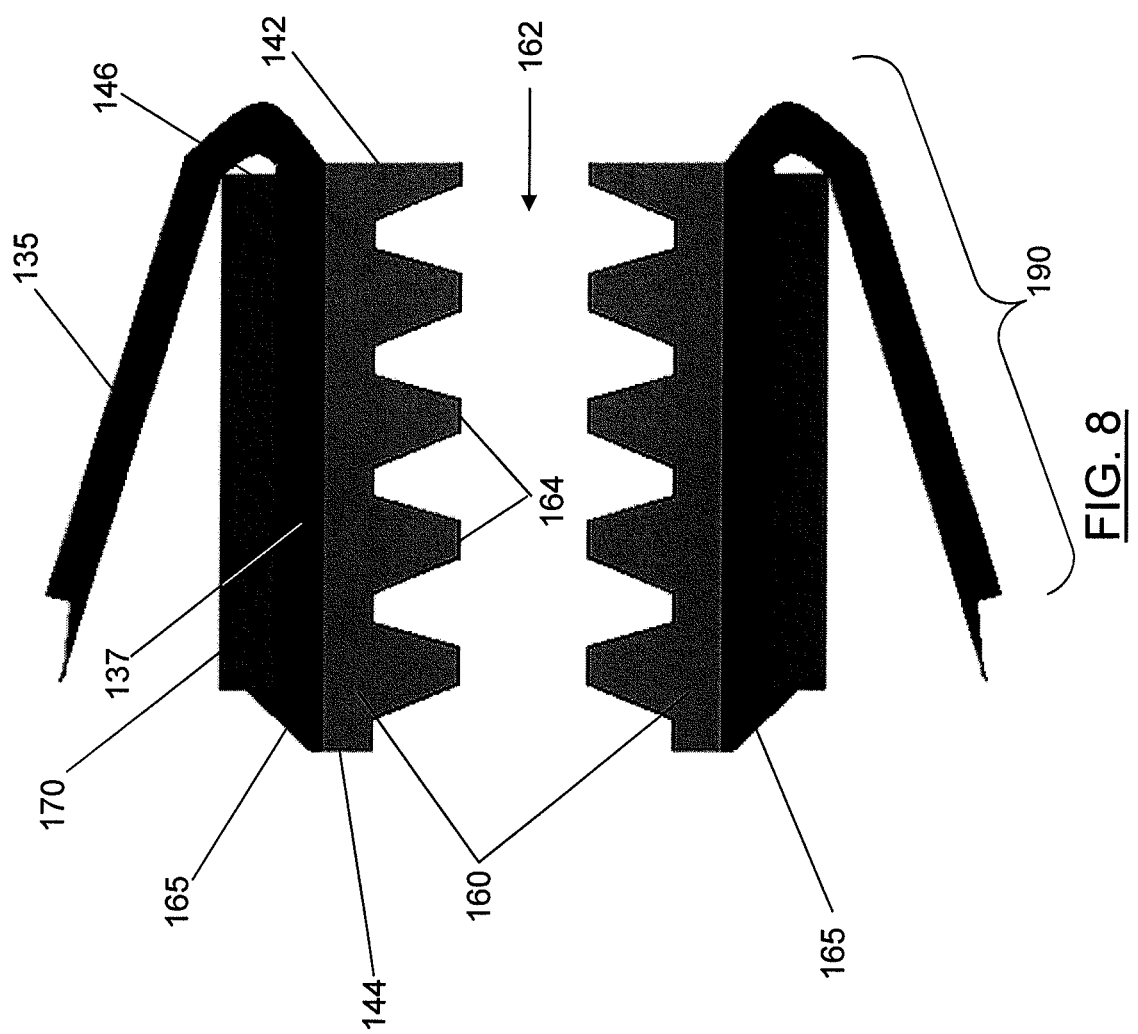
FIG. 8 is a close-up cross-sectional view of a first end feature of the medical device according to an exemplary embodiment.
Figure 10:
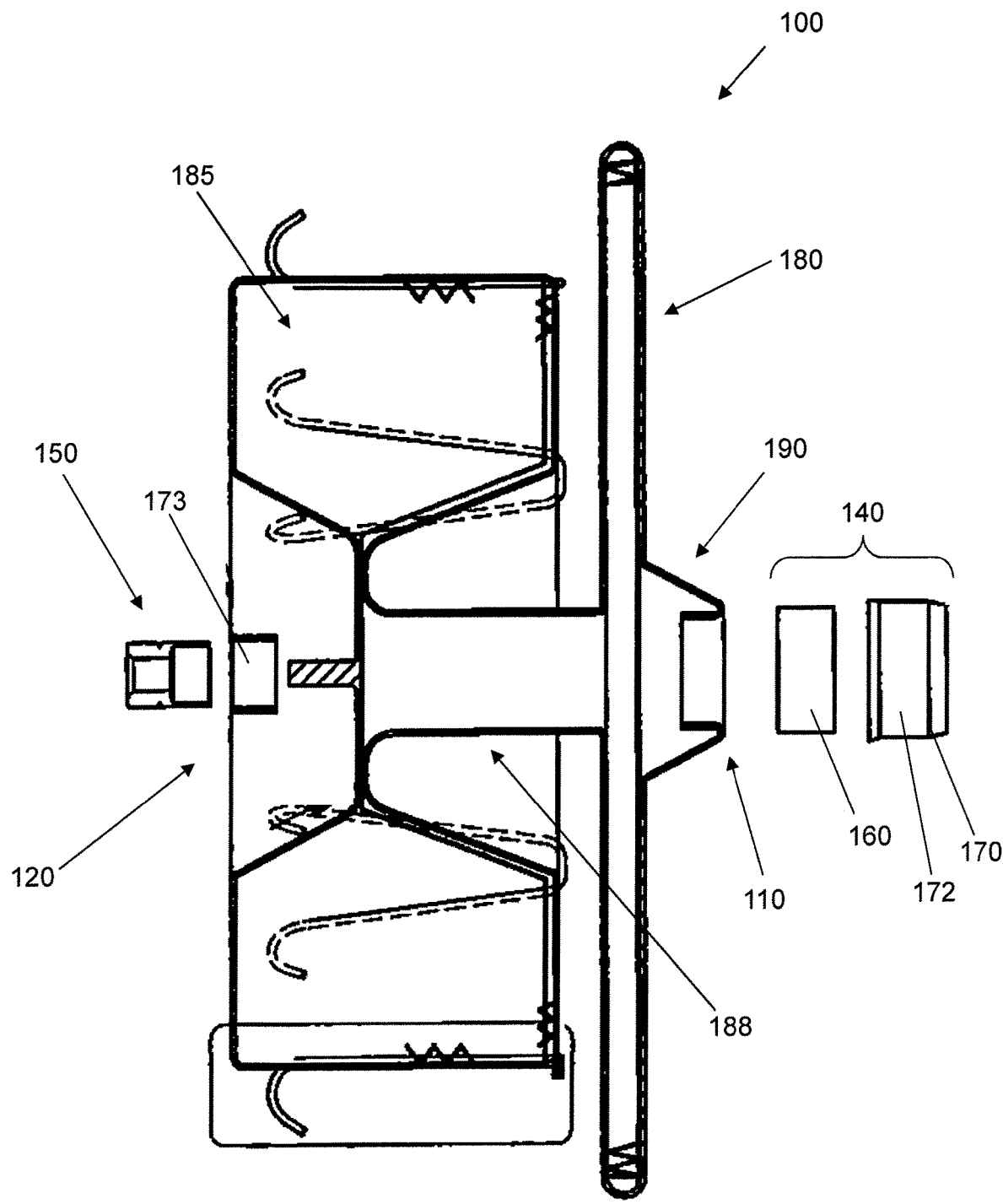
FIG. 10 is a simplified cross-sectional view of the medical device of FIG. 6 in exploded form according to an exemplary embodiment.

A simplified cross-section of one embodiment of the medical device is shown in FIG. 6, with a more detailed cross-section depicting the braided strands from which the tubular structure is formed shown in FIG. 7. A simplified exploded view of the medical device 100 is shown in FIG. 10. With reference to FIGS. 4, 6, 7, and 10, embodiments of the medical device 100 comprise a tubular structure 130 comprising a plurality of braided strands 135 including proximal strand ends 137. A first end feature 140 is provided that includes a proximal end 142 and a distal end 144. The first end feature 140 may be configured to receive and secure the proximal strand ends 137 via the proximal end of the first end feature. In some cases, as shown in FIGS. 8 and 10, the first end feature 140 may include an inner bushing 160 (e.g., a stainless steel bushing) in which an inner lumen 162 is formed, and internal threads 164 may be defined on an inner surface of the threaded inner bushing 160 for receiving corresponding threads of a pusher wire of a delivery system, for example. The plurality of strands 135 may be placed around the threaded inner bushing 160, as shown, and another, larger diameter outer bushing 170 (e.g., a platinum/iridium alloy bushing) may be disposed around the inner bushing 160, such that the proximal ends 137 of the braided strands 135 are secured (e.g., tightly wedged) between the inner and outer bushings 160, 170. The proximal ends 137 of the braided strands 135 may then be secured, e.g., by laser welding such that a weld 165 is created to fuse both the inner and outer bushings 160, 170 to the strands 135. The braid may then be inverted (e.g., by reversing the braiding direction) so that when the medical device 100 is formed, the first end feature 140 is recessed from the proximal end 110 of the device, as shown, and is internal to the medical device.

With reference to FIG. 10, the first end feature 140 may comprise a marker band 172 on an external surface of the outer bushing 170 that is configured to facilitate placement of the medical device 100 at the target site. For example, the marker band 172 may include a radiopaque material, such as a platinum iridium alloy, to allow a medical practitioner to view the location of the medical device 100 (and, more particularly, the location of the proximal end 110 of the medical device) within the body using radio fluoroscopy to facilitate proper delivery and positioning of the device. In some cases, however, the outer bushing 170 itself is made of a radiopaque material, such that the bushing serves as the marker band.

Referring again to FIGS. 4, 6, 7, and 10, the tubular structure 130 may comprise an expanded volume portion 180 proximate the first end feature and a tapered transition portion 190 extending between the expanded volume portion 180 and the proximal end 142 of the first end feature 140. For example, the inversion of the braid at the proximal end 142 of the first end feature 140 (FIG. 8) may serve to create the tapered transition portion 190. In the expanded state (e.g., shown in FIG. 2), the expanded volume portion 180 of the tubular structure may have an expanded volume diameter $D_e$, and the tapered transition portion 190 may define a first transition diameter $D_1$ proximate the expanded volume portion and a second transition diameter $D_2$ proximate the proximal end 142 of the first end feature 140. As shown, the first transition diameter $D_1$ may be greater than the second transition diameter $D_2$, but smaller than the expanded volume diameter $D_e$. Moreover, the first transition diameter $D_1$ may be disposed between the second transition diameter $D_2$ and the expanded volume diameter $D_e$, and the second transition diameter $D_2$ may be substantially equal to a diameter of the first end feature 140.

Figure 3:
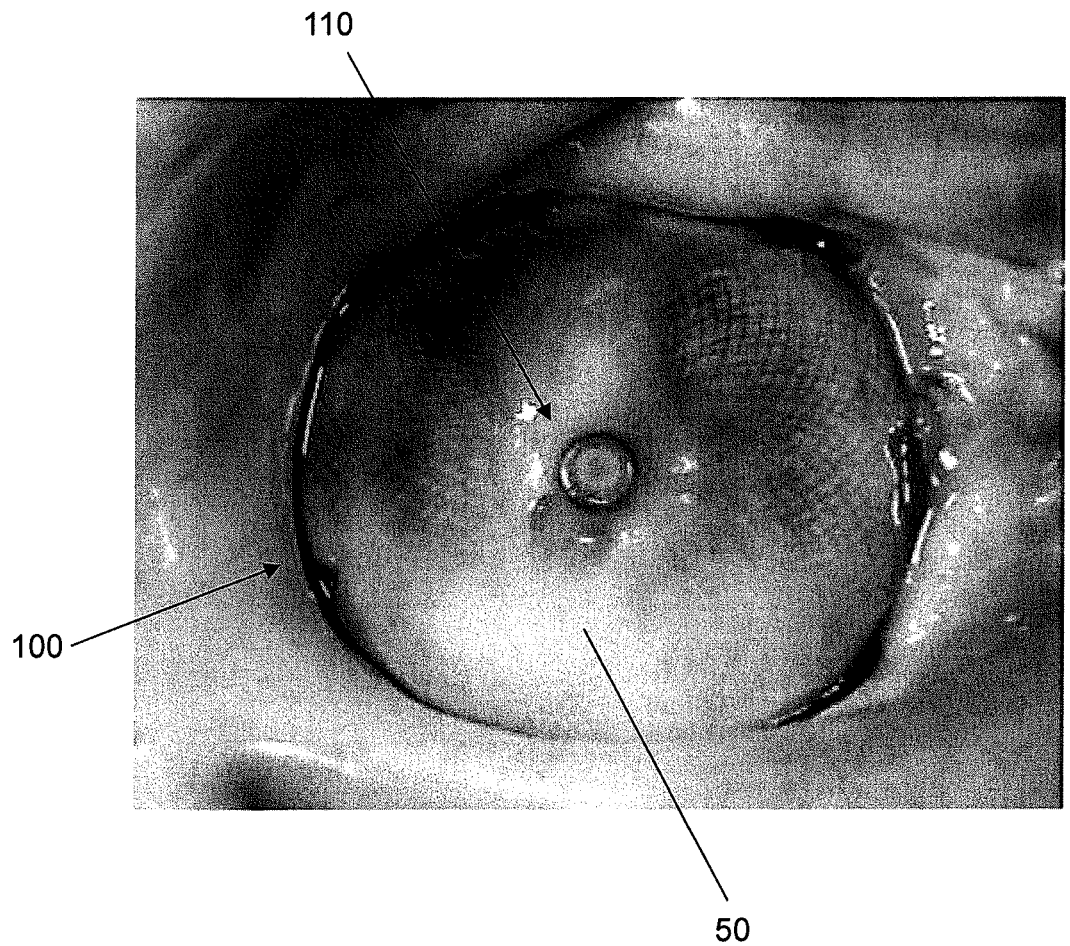
FIG. 3 illustrates tissue growth over the proximal end of an implanted medical device according to an exemplary embodiment.
Figure 10A:
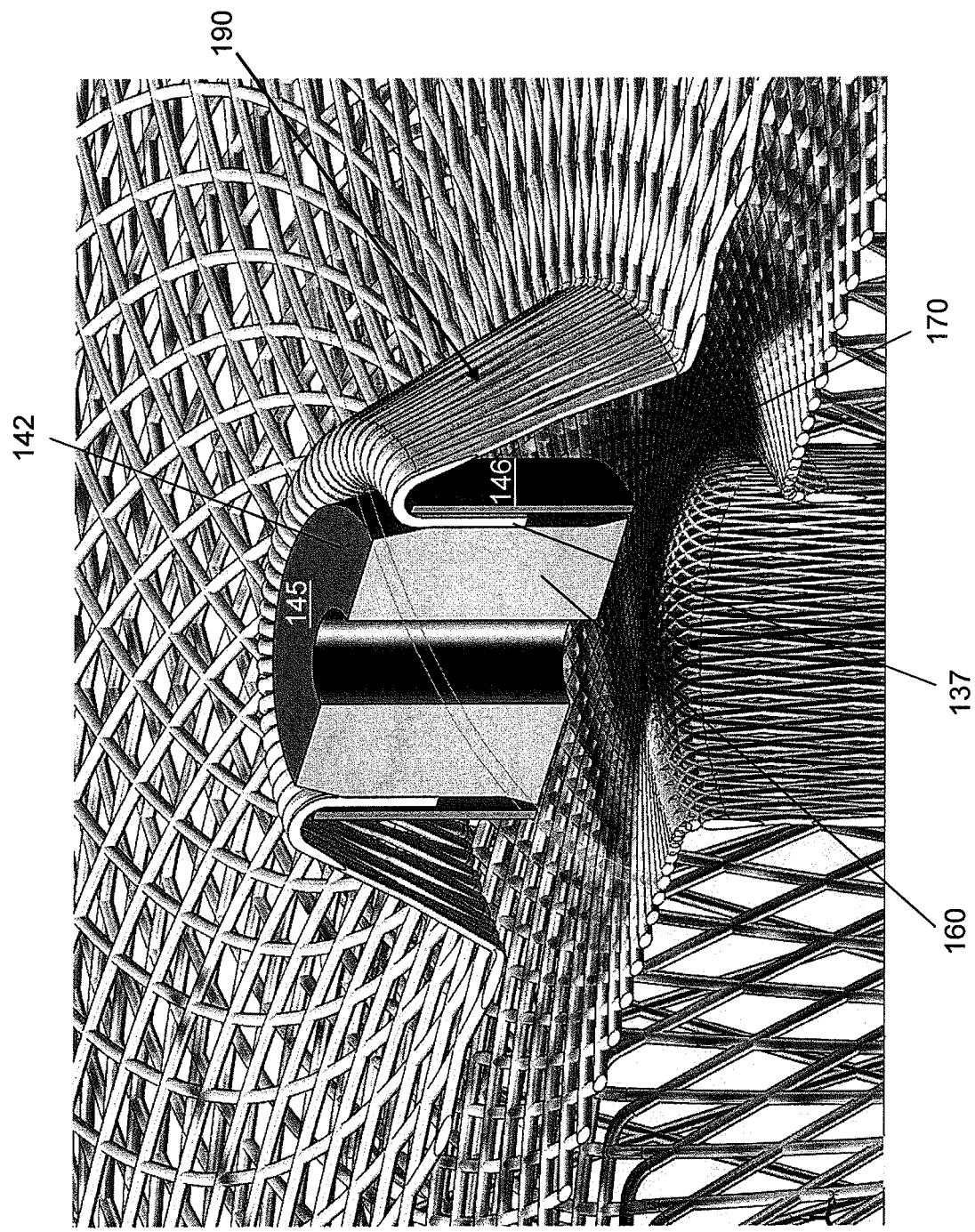
FIG. 10A is a perspective cross-sectional view of the first end feature of the medical device of FIG. 10 according to an exemplary embodiment.

The tapered transition portion 190 may be configured such that the second transition diameter $D_2$ is sized to allow tissue growth over the proximal end 110 of the medical device 100, as shown in FIG. 3. Said differently, because the proximal end 142 of the first end feature 140 substantially coincides with the proximal end 110 of the medical device 100, the proximal end 110 of the medical device has a small smooth surface (e.g., as compared to the protruding end clamp 20 of the conventional medical device 10 shown in FIG. 1) that allows and facilitates rapid tissue growth over the surface to minimize the chance of a thrombotic embolus being released from the device. For example, as shown in FIG. 10A, the first end feature 140 may include a proximal end surface 145, a distal end surface (not visible), and a circumferential surface 146 extending between the proximal and distal surfaces. Because of the way the proximal strand ends are secured to the first end feature (as depicted in the figures), the transition portion 190 substantially surrounds the circumferential surface, such that only the proximal end surface (or a portion of the proximal end surface) of the first end feature 140 is exposed to fluid flow through the body lumen.

Figure 11:
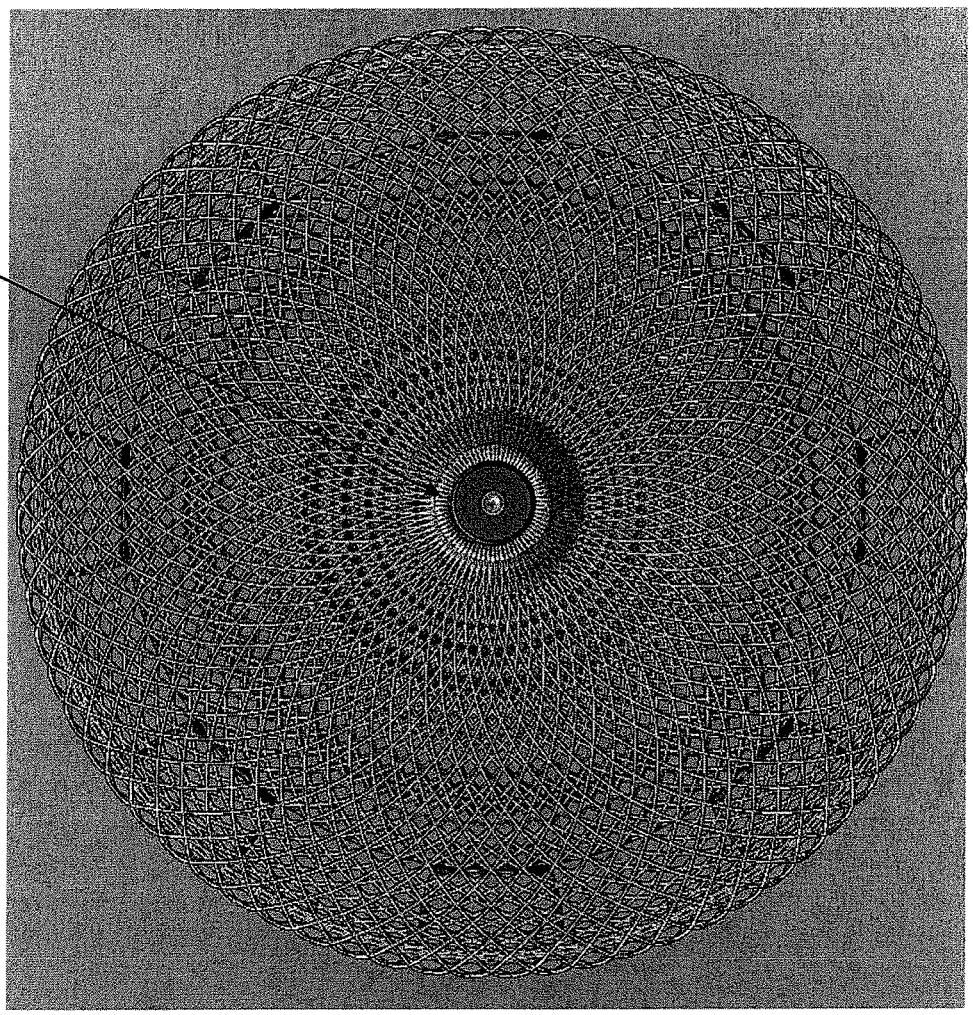
FIG. 11 illustrates the proximal end of a medical device according to an exemplary embodiment.
Figure 12:
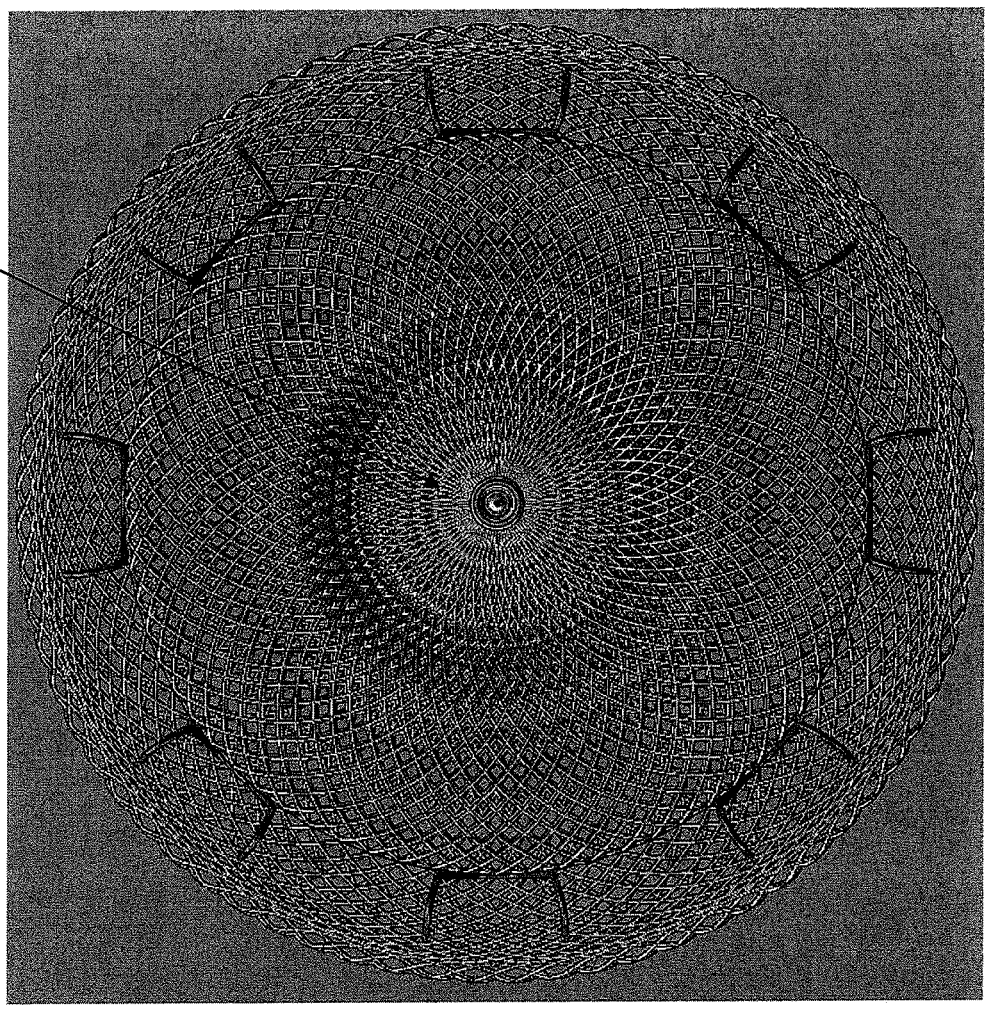
FIG. 12 illustrates the distal end of a medical device according to an exemplary embodiment.

With reference to FIGS. 6 and 7, the medical device 100 may further comprise a second end feature 150 that is configured to receive and secure distal strand ends 138 (FIG. 6) of the plurality of braided strands. The second end feature 150 may, for example, define a proximal end 152 and a distal end 154, and the proximal end 152 of the second end feature 150 may define an opening at least partially therethrough. The opening at the proximal end 152 of the second feature 150 may be configured to receive the distal strand ends 138 and may secure them together and/or to the second end feature 150. For example, the second end feature 150 may be configured to hold the distal strand ends together 138 by clamping, welding, soldering, brazing, or otherwise adhering them to each other and/or to the second end feature 150. The second end feature 150 may also include a marker band 173 (FIG. 10) to help locate the distal end 120 of the medical device 100, as noted above with respect to the first end feature 140. Views of the proximal and distal ends 110, 120 of the medical device are shown in FIGS. 11 and 12.

In some embodiments, however, not shown, the second end feature 150 may be configured similarly to the first end feature 140, in that the second end feature 150 may be configured to receive and secure the distal strand ends 138 via the distal end 154 of the second end feature. Thus, the distal end 154 of the second end feature 150 may substantially coincide with the distal end 120 of the medical device 100, which may allow tissue to grow over the surface of the distal end 120 without creating thrombus as noted above with respect to the first end feature 140. Such a configuration for both the first and second end features 140, 150 may be especially useful in cases in which both the proximal and distal ends 110, 120 of the medical device 100 are to be exposed to transverse blood flow.

The medical device 100 may have various configurations depending on factors such as the type of abnormality to be occluded, the location of the target site, the condition of the patient's vasculature, and the practitioner's preferences. For example, in the depicted embodiment of FIG. 7, the medical device 100 has an expanded volume portion 180 proximate the first end feature that defines at least one surface (in this case, two surfaces 182, 184) that are substantially perpendicular to a central axis A extending between the first end feature 140 and the second end feature 150. Moreover, the expanded volume portion 180 may be a first expanded volume portion, and a second expanded volume portion 185 may be provided proximate the second end feature 150 that is displaced axially from the first expanded volume portion 180. In some cases, as noted above, the tapered transition portion 190 may be a first transition portion, and a second transition portion may be defined that extends between the second expanded volume portion 185 and the second end feature 150 (not shown).

As depicted in FIG. 7, the expanded volume portion 180 may be generally disk shaped, for example, to facilitate maintaining the medical device 100 in position at the target site, as described in greater detail below. The second expanded volume portion 185 may, in some cases, be a generally cylindrically shaped portion that is axially disposed toward the second end feature 150 (e.g., distally from the first end feature 140 and/or the first expanded volume portion 180). In some cases, the second expanded volume portion 185 may be sized to be somewhat larger in diameter (e.g., about 10-30%), than the inside diameter of the vessel, cavity, or lumen to be occluded. This sizing may be intended to facilitate anchoring the device to prevent dislodgement.

At the same time, the first expanded volume portion 180 of the device 100 may have a diameter that is intended to abut the adjacent wall surrounding the abnormal aperture to prevent device movement toward the second expanded volume portion 185 and to assist in sealing the aperture. For example, the first expanded volume portion 180 may be oversized so as to be capable of overlying the ostium or opening of the LAA and lying adjacent to, and in flush contact with, the wall of the atrium. The diameter of the second expanded volume portion may be less than the diameter of the first volume portion so as to fit in the LAA. The first expanded volume portion 180 may also be flexible so as to be capable of conforming to the curvature of the wall of the atrium in LAA applications or other vascular structures in other applications. Although one configuration of the first and second expanded volume portions 180, 185 is described above and shown in the figures, various other configurations and sizes may be used depending on the particular application or condition to be treated. For example, one or both expanded volume portions 180, 185 may be flat disks or disks having a convex distal end, or the device may include a smaller diameter central cylindrical portion between two larger diameter disks. Moreover, the depth or thickness of the first and/or second expanded volume portions may depend on the thickness and number of layers used to make the medical device 100.

In some embodiments, the tubular structure 130 may further include a flexible connecting portion 188 that extends between and connects the first expanded volume portion 180 and the second expanded volume portion 185. The flexible connecting portion 188 may define, for example a narrower connecting diameter $D_3$ (FIG. 2) with respect to the diameters of the first and second expanded volume portions 180, 185, such that the first expanded volume portion 180 is allowed to articulate (e.g., pivot) relative to the second expanded volume portion 185. In this way, the relative positions of the first and second expanded volume portions 180, 185 may be adjustable to accommodate different target sites and configurations (e.g., size and location) of abnormal openings to be occluded. Furthermore, the second expanded volume portion 185 may define a conical surface 189 from which the flexible connecting portion 188 extends, as shown in FIG. 7. The conical surface may allow the distance between the first expanded volume portion 180 and the second expanded volume portion 185 to vary and may thus provide a way of creating tension between the expanded volume portions and retention hooks (described below) to maintain the first expanded volume portion 180 over the ostium and keep the device in place.

Referring now to FIGS. 2 and 4, in some embodiments, the medical device 100 may include retention hooks 200. The retention hooks 200 may be fabricated from Nitinol wire that is heat set into a hook shape at each end and has a bend 205 (FIG. 2), e.g., a bend of less than about 180 degrees, in the mid length segment of the wire so as to create two interconnected hooks. The hooks 200 may also at least partially extend within the medical device 100 in some cases (not shown). In the depicted embodiments, the hooks 200 are disposed on the second expanded volume portion 185, and the ends 210 of the hooks 200 extend radially out from the second volume portion and are oriented toward the first expanded volume portion 180. For example, the hooks 200 may be sutured, woven, fastened, or otherwise attached to the braided fabric forming the second expanded volume portion 185.

According to one embodiment, the wires of the hooks 200 may be about 0.003-0.007 inches in diameter and 2-10 mm in length and may be flexible enough to be back loaded into a delivery catheter or forward loaded if introduced in a straightened-out configuration. The medical device 100 may have any number of hooks 200, and in some cases three to twelve pairs of hooks may be provided, such as eight pairs of hooks. The hooks 200 may thus be configured to assist in the retention of the medical device 100 by resisting motion of the device in the vessel in a direction that would cause the hooks to engage the tissue. In other words, the hooks 200 are configured to engage body tissue when the medical device 100 is moved along its axis A in the proximal direction. In the depicted embodiment, the hooks 200 do not have barbs so that the engagement with the tissue is reversible by movement of the medical device 100 in a distal direction. Moreover, in LAA applications, for example, the hooks 200 may be configured to penetrate the wall of the LAA, but would not extend completely through the wall of the LAA. Thus, the hooks 200 may reduce the incidence of effusion by not puncturing through the wall of the LAA.

In some embodiments, the hooks 200 may be integral to the medical device 100, such as when individual strands of the braided tubular structure 130 are isolated, cut, and a short portion of the wire adjacent the cut formed into an outward projecting hook. Such a configuration may provide for a medical device 100 that has a significantly lower profile as no added material (e.g., no separate hooks) contributes to the collapsed overall diameter $D_c$ (FIG. 5) of the medical device during passage through a delivery catheter. In addition, through the use of integral hooks 200 there are no added suture materials or suture knots that are needed to attach the hooks to the braided tubular structure, which also translates into a reduced profile of the medical device.

As noted above, the second expanded volume portion 185 may be oversized so that it will engage the lumen of the vessel, body organ, or the like to be occluded. The medical device 100 may then be held in place by the combination of the radial engagement of the second expanded volume portion 185 with the lumen of the vessel, body organ, or the like and the engagement of the hooks 200 with the vessel wall. Over a relatively short period of time, thrombi will form in and on the medical device 100 and occlude the lumen. Although the first and second expanded volume portions 180, 185 may be various sizes, the first expanded volume portion may be at least about 10% larger in diameter than the second expanded volume portion according to one embodiment.

For example, in the case of a medical device 100 that is implanted within the LAA, the medical device 100 may be positioned such that the first expanded volume portion 180 overlies the ostium of the LAA, while the second expanded volume portion 185 is positioned within the LAA. Thus, the first expanded volume portion 180 may be sized and configured to ensure that the first expanded volume portion 180 is implanted to a predetermined depth within the LAA. The second expanded volume portion 185 may in turn be sized and configured to self expand and engage the wall of the LAA, and the hooks 200 may be configured to penetrate into the wall of the LAA, as explained below. Over time, thrombi will form in and on the first and second expanded volume portions 180, 185 to occlude the LAA.

Figure 9:
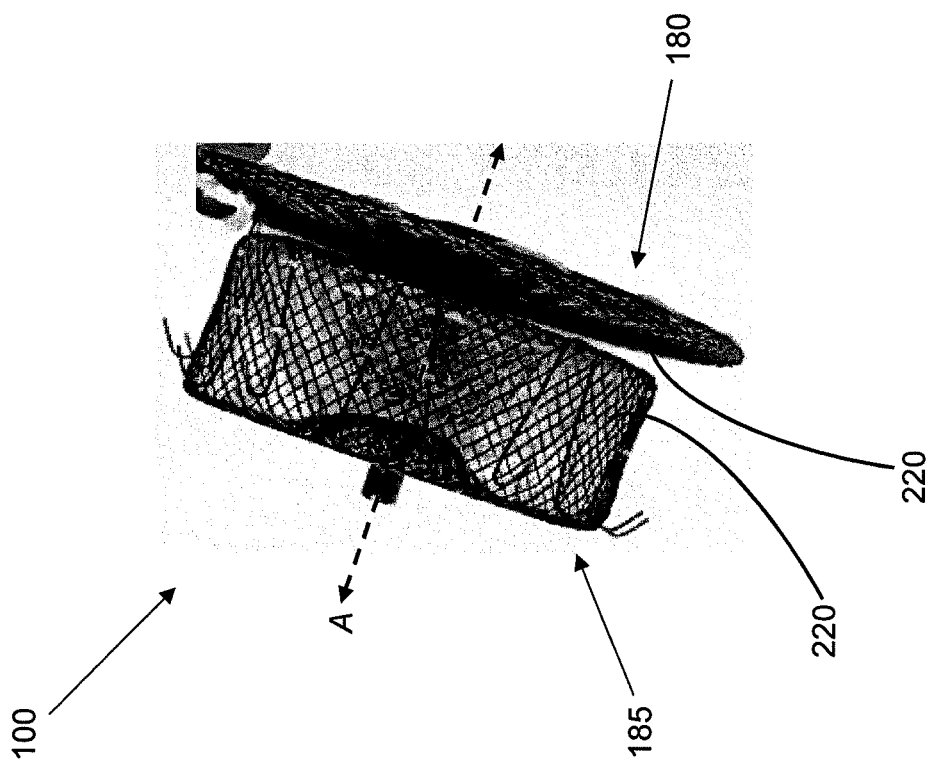
FIG. 9 illustrates a medical device that includes a polymer fabric in each of the first and second expanded volume portions according to an exemplary embodiment.

In some embodiments, in order to speed up the occlusion of the medical device 100, the medical device may be at least partially coated with a suitable thrombogenic agent, filled with a fiber (e.g., a polymer fabric), braided with an increased number of strands, or include multiple layers of braided strands. For example, the medical device 100 may include one or more layers of polymer fabric 220 positioned within the first and/or second expanded volume portions 180, 185, as shown in FIG. 9. In particular, one or more layers of polymer fabric 220 may be sized and configured to be positioned within each of the first and second expanded volume portions 180, 185, such that the polymer fabric extends substantially perpendicularly to the axis A of the medical device 100. Each piece of polymer fabric 220 may be sutured circumferentially about its periphery and about the inner circumference of the first and second expanded volume portions 180, 185, respectively. The polymer fabric 220 may be flexible and may be easily collapsed with the medical device 100 for delivery through a catheter. In this way, the interwoven fiber (which in some embodiments may be polyester) may attach to a clot to retain the clot firmly within the device as it forms the occlusion.

Figure 13:
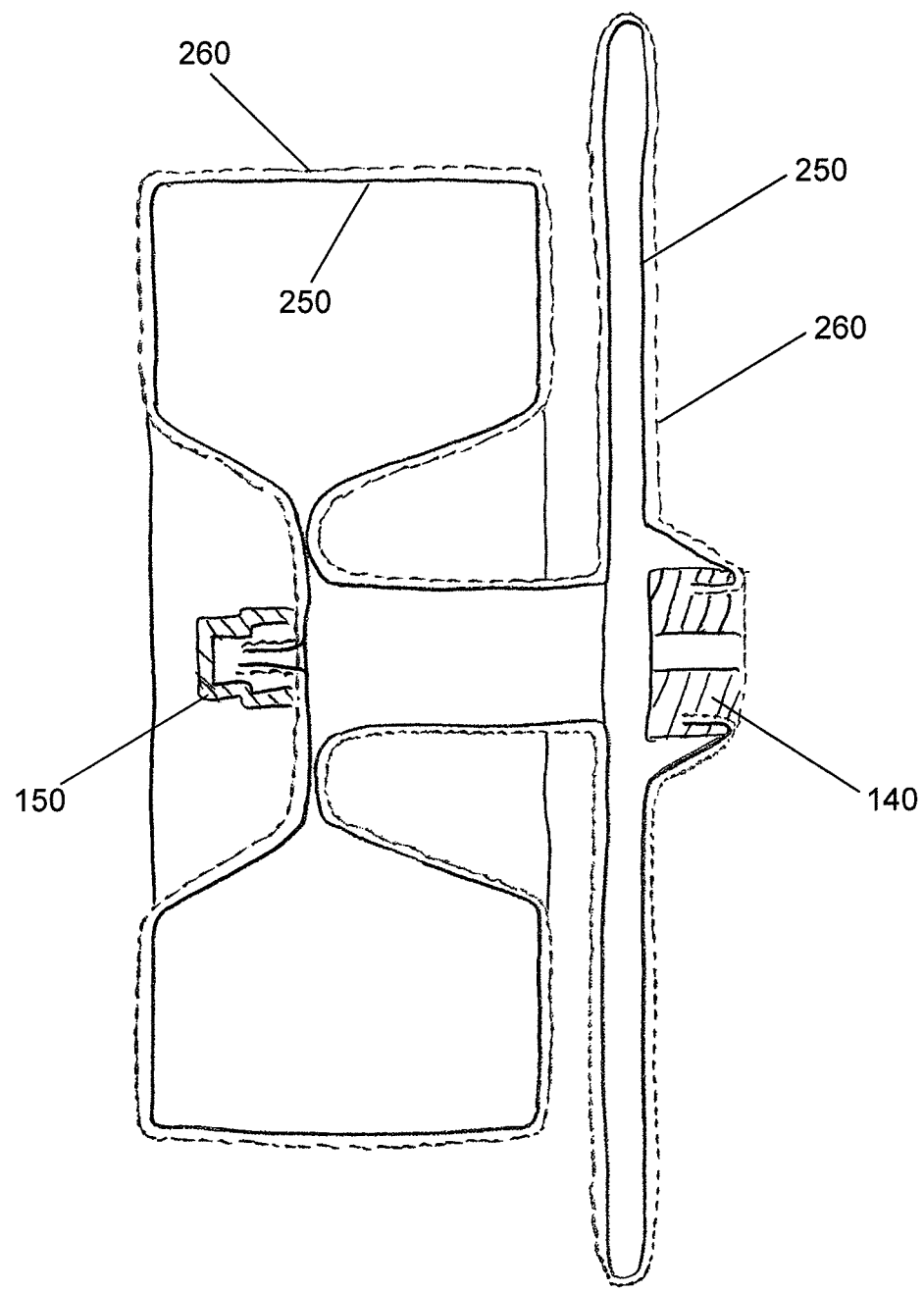
FIG. 13 is a schematic illustration of a medical device including first and second tubular structures (an inner and an outer layer) according to an exemplary embodiment.

Although the embodiments depicted in FIGS. 2-12 show a medical device having a single layer of braided fabric (e.g., a single tubular structure 130), in some cases a second plurality of strands may be braided to form a second tubular structure, such that medical device includes an inner and outer layer. Referring FIG. 13, for example, the medical device 100 may include an inner layer 250 and an outer layer 260. The inner layer 250 may be disposed adjacent to the outer layer 260, and in some cases the inner layer may have a different shape than the outer layer. The first and second expanded volume portions 180, 185 and the connecting portion 188 may be integrally formed from the same tubular structure.

In some embodiments, the pick count, or the number of strand crossings per unit length of the layers 250, 260, may be set at the same or different predetermined values. For example, the inner layer 250 may define a first pick count, and the outer layer 260 may define a second pick count, where the second pick count is different from the first pick count. Although the first pick count, as braided, may be different from the second pick count, as braided, the first and second pick counts may be selected such that the relationship between the reduction in diameter and the elongation of the inner layer 250 is substantially the same as the relationship between the reduction in diameter and the elongation of the outer layer 260 as the medical device 100 is moved between the expanded and contracted states. For example, a ratio of the decrease in diameter of the inner layer 250 to the increase in length of the inner layer 250 may be substantially the same as a ratio of the decrease in diameter of the outer layer 260 to the increase in length of the outer layer 260. Thus, adjacent portions of the inner and outer layers 250, 260 may remain in their relative adjacent positions as the medical device 100 is moved between the expanded and contracted states. In this way, the inner layer 250 and the outer layer 260 of the medical device 100 may cooperatively collapse and expand at generally the same rate, which enhances the stability of the medical device and facilitates its delivery into the vessel lumen and subsequent self-expansion. In the case where the inner and outer layers have different shapes from one another, the pick count of each layer may be selected such that in the elongated, contracted state each layer is substantially the same length.

Furthermore, the helix angle of the strands (e.g., the angle formed between the strand and the longitudinal axis of the braid mandrel as the strand is applied to the mandrel) used to braid the plurality of strands of the inner and outer layers 250, 260 may be the same or different. The helix angles may be selected such that the plurality of strands of the inner layer 250 is braided at a first helix angle, and the plurality of strands of the outer layer 260 is braided at a second helix angle to ensure that the relationship between the reduction in diameter and the elongation of the inner layer is substantially the same as the relationship between the reduction in diameter and the elongation of the outer layer as the at least one layer is moved between the expanded state and the contracted state. In the case where the inner and outer layers have different shapes from one another, the helix angle of each layer may be selected such that in the elongated, contracted state each layer is substantially the same length.

As noted above, the uniform movement that results between the inner and outer layers 250, 260 may thus reduce the risk of bunching or gathering of the layers within the medical device 100, which would otherwise reduce the effectiveness of the medical device by increasing its delivery profile and/or generating gaps between the various layers of material that may cause leaks.

The plurality of strands forming the second tubular structure may be made of the same or different material as the strands forming the first tubular structure, described above. Thus, the strands of the second tubular structure may be comprised of metal or polymer material. For example the second tubular structure may be made of stainless steel, other metallic alloys, highly elastic alloys, and/or shape memory alloys, which are both resilient and can be heat treated to substantially set a desired shape, as noted above with respect to the first tubular structure. In addition, polymeric materials may be combined with other materials in the formation of tubular structures for certain applications. For example, the medical device 100 may include a combination of polyester strands and stainless steel wire. Thus, in some embodiments, the plurality of braided strands of the inner layer 250 may include Nitinol, and the plurality of braided strands of the outer layer 260 may include a polymer, or vice versa.

A method for making a medical device for placement in a body lumen as described above is summarized in FIG. 14. The method includes braiding a plurality of strands defining proximal strand ends to form a tubular structure at Block 300 and attaching a first end feature defining a proximal end and a distal end to the proximal strand ends via the proximal end of the first end feature at Block 310. As described above with reference to the figures, the tubular structure may define a molded and heat set resilient expanded volume portion proximate to the first end feature and a tapered transition portion extending between the expanded volume portion and the proximal end of the first end feature. In the expanded state, the expanded volume portion of the tubular structure may define an expanded volume diameter, and the tapered transition portion may define a first transition diameter proximate the expanded volume portion and a second transition diameter proximate the proximal end of the first end feature. As described above and illustrated in the referenced figures, the first transition diameter may be greater than the second transition diameter, smaller than the expanded volume diameter, and disposed between the second transition diameter and the expanded volume diameter. The second transition diameter may be substantially equal to a diameter of the first end feature. In this way, the first end feature may be substantially surrounded by the tapered transition portion, such that the proximal end of the first end feature substantially coincides with the proximal end of the medical device.

As noted above, a second end feature defining a proximal end and a distal end may be attached to the distal strand ends. Block 320. In some cases, the second end feature may receive the distal strand ends via the proximal end of the second feature, as shown in the figures, whereas in other cases the second end feature may receive the distal strand ends via the distal end of the second end feature similar to the first end feature, thereby also keeping the second end feature from protruding from the distal end of the medical device. The medical device may be modified and configured in various other ways, such as by attaching retention hooks to the tubular structure (e.g., to the outside of second expanded volume portion) (Block 330), including a polymer fabric in one or more of the expanded volume portions (Block 340), and/or coating the device with a thrombogenic agent (Block 350), as described in greater detail above.

Figure 17:
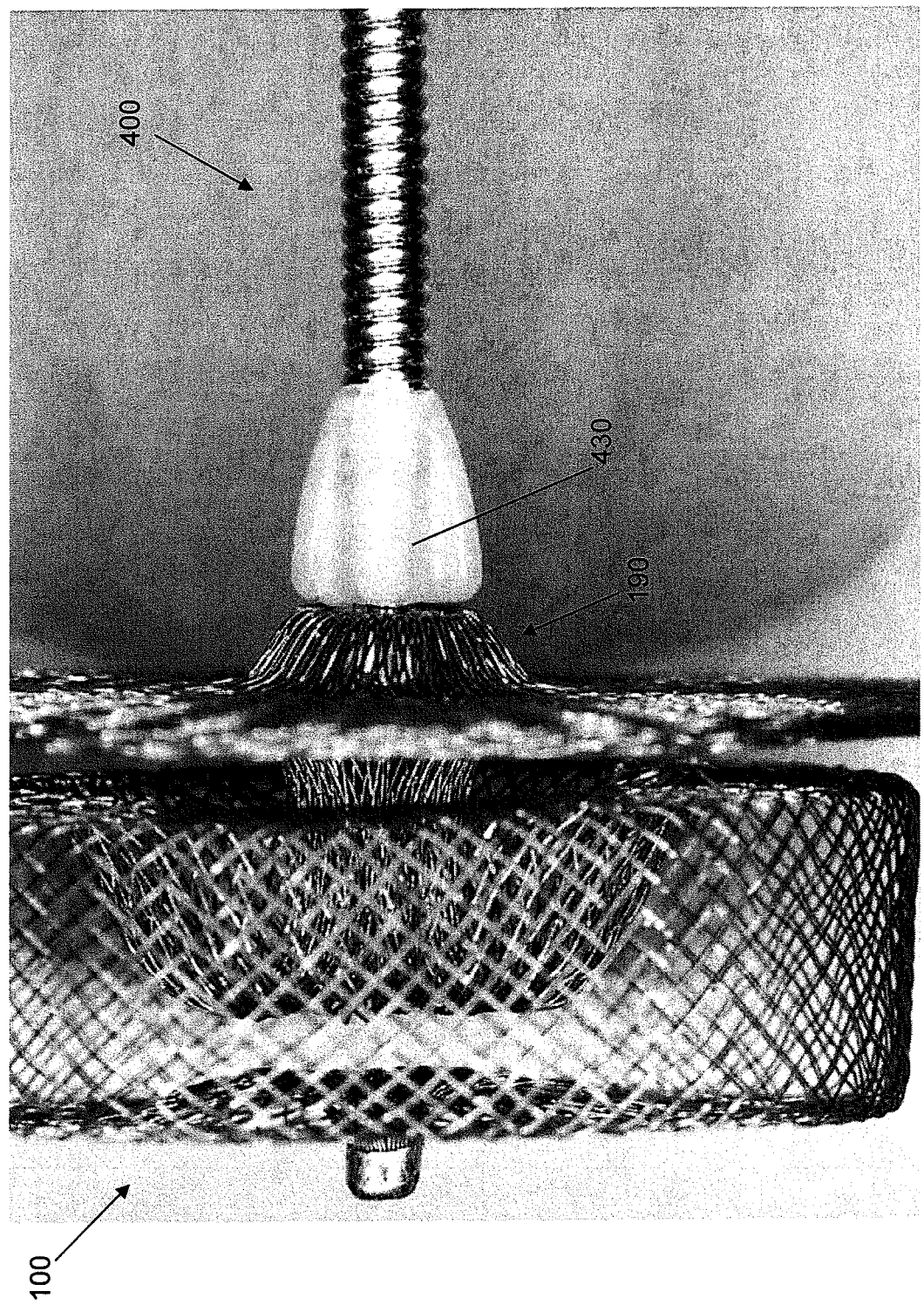
FIG. 17 is a schematic illustration of the delivery device of FIG. 15A engaged to the proximal end of the medical device according to an exemplary embodiment.

Referring now to FIGS. 15A, 15B, 16, and 17, a delivery device 400 may be provided for deploying embodiments of the medical device 100 described above. The delivery device 400 may include an inner pusher wire 410 with a distal end 415 defining external threads. The external threads of the pusher wire 410 may be configured to engage corresponding internal threads 164 of the first end feature 140 (shown in FIG. 8) so as to releasably attach the medical device 100 to the delivery device 400 for delivery to and deployment at the target site, as illustrated in FIG. 17.

The delivery device 400 may further include an outer member 420 defining a lumen through which the inner pusher wire 410 is slideably received. In other words, the inner pusher wire 410 may be axially moveable within the outer member 420, such that the inner pusher wire may be moved between the position shown in FIG. 15A and FIG. 15B, for example. A distal end of the outer member 420 may include a guide member 430 configured to guide the proximal end 110 of the medical device into a distal end of a delivery sheath 440. In some cases, the guide member 430 may be made of a polymer material. The guide member 430 may have a tapered external surface, such that the diameter $D_d$ of the guide member at its distal end is approximately the same as (e.g., slightly less than) the inner diameter of the delivery sheath 440 and the diameter $D_p$ of the guide member at its proximal end is approximately the same as (e.g., slightly greater than) the outer diameter of the outer member 420. Moreover, as shown in FIG. 17, the distal diameter $D_d$ of the guide member may approximate the second transition diameter $D_2$ of the transition portion 190, such that the taper of the transition portion 190 and the guide member generally correspond to one another. In some cases, as shown, the outer surface of the guide member 430 may include grooves or concavities 431, which may serve to prevent the taper of the guide member from acting as a plunger that draws air into the delivery sheath 440 from the proximal end as the medical device 100 is advanced to toward the distal end 445. In other words, the concavities 431 may allow fluid to flow through the delivery sheath 440, such that a positive blood pressure exists in the delivery sheath with respect to the pressure outside the body.

The function of the guide member 430 may be illustrated by the following example. When accessing a tortuous path (e.g., a vessel that includes one or more small radius curves), the pusher wire 410 and/or the outer member 420 may be biased to one side of the delivery sheath 440 once the medical device 100 has been deployed (e.g., is outside the delivery sheath 440, but still attached to the pusher wire 410). In some cases, the medical device 100 must be recaptured within the delivery sheath 440, for example, to reposition the medical device at the target site or to replace the device for one of a different size. As the medical device 100 is moved proximally (closer) to the distal end 445 of the delivery sheath 440 during recapture, the medical device 100 may not be axially aligned with the lumen of the delivery sheath (e.g., as a result of the curvature of the vessel within which the delivery sheath is disposed). The guide member 430, by virtue of its tapered shape, may thus bring the proximal end 110 of the medical device 100 into closer axial alignment with the lumen of the delivery sheath to allow for easier recapture and to minimize the risk of damaging the medical device during recapture.

Figure 18:
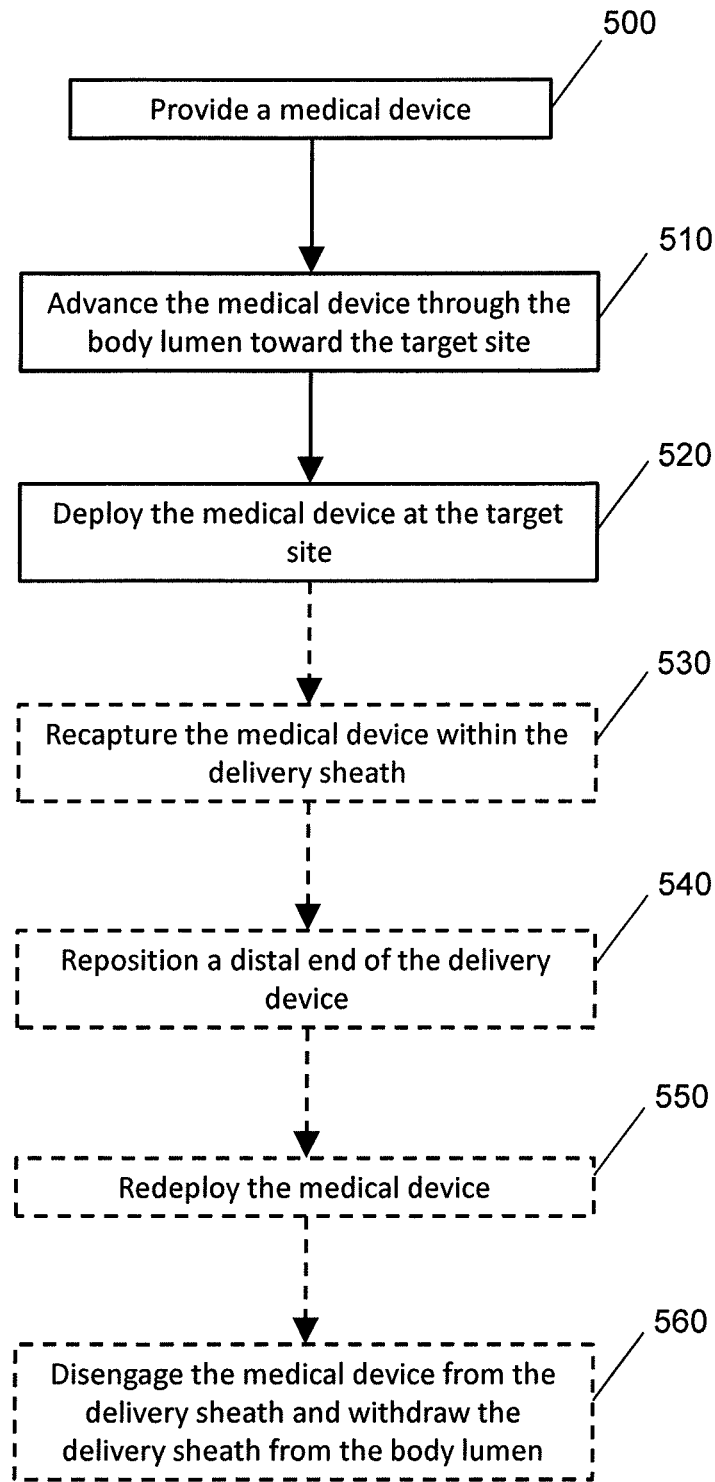
FIG. 18 illustrates a flowchart for a method for delivering a medical device.

Accordingly, in FIG. 18, a method for delivering a medical device as described above is summarized. The method includes providing a medical device configured as described above in connection with one or more of FIGS. 2-17. Block 500. For example, the medical device may include a tubular structure comprising a plurality of braided strands defining proximal strand ends and a first end feature defining a proximal end and a distal end, where the first end feature is configured to receive and secure the proximal strand ends via the proximal end of the first end feature. As described above, the tubular structure may define one or more expanded volume portions and at least one tapered transition portion.

The method of delivery may further include advancing the medical device through the body lumen toward the target site (Block 510) and deploying the medical device at the target site (Block 520). In some cases, as described above, the method may further include recapturing the medical device within the delivery sheath (Block 530), repositioning a distal end of the delivery device (Block 540), and redeploying the medical device (Block 550). Once the medical device is positioned at a desired location, the delivery device may be disengaged from the medical device (e.g., via unthreading the medical device from the pusher wire) and withdrawn from the body lumen, leaving the medical device in place at the target site. Block 560.

Figure 14:
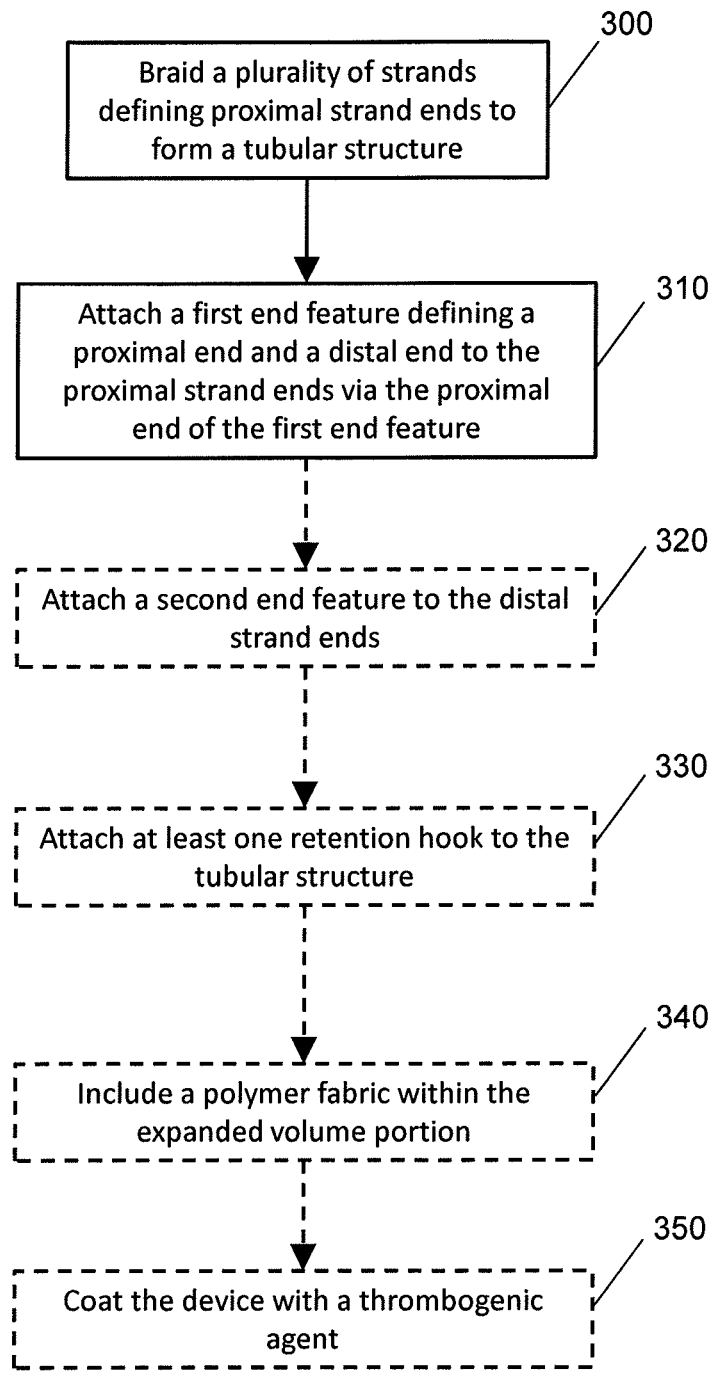
FIG. 14 illustrates a flowchart for a method for making a medical device for occluding an abnormal opening in the body lumen.
Figure 15A:
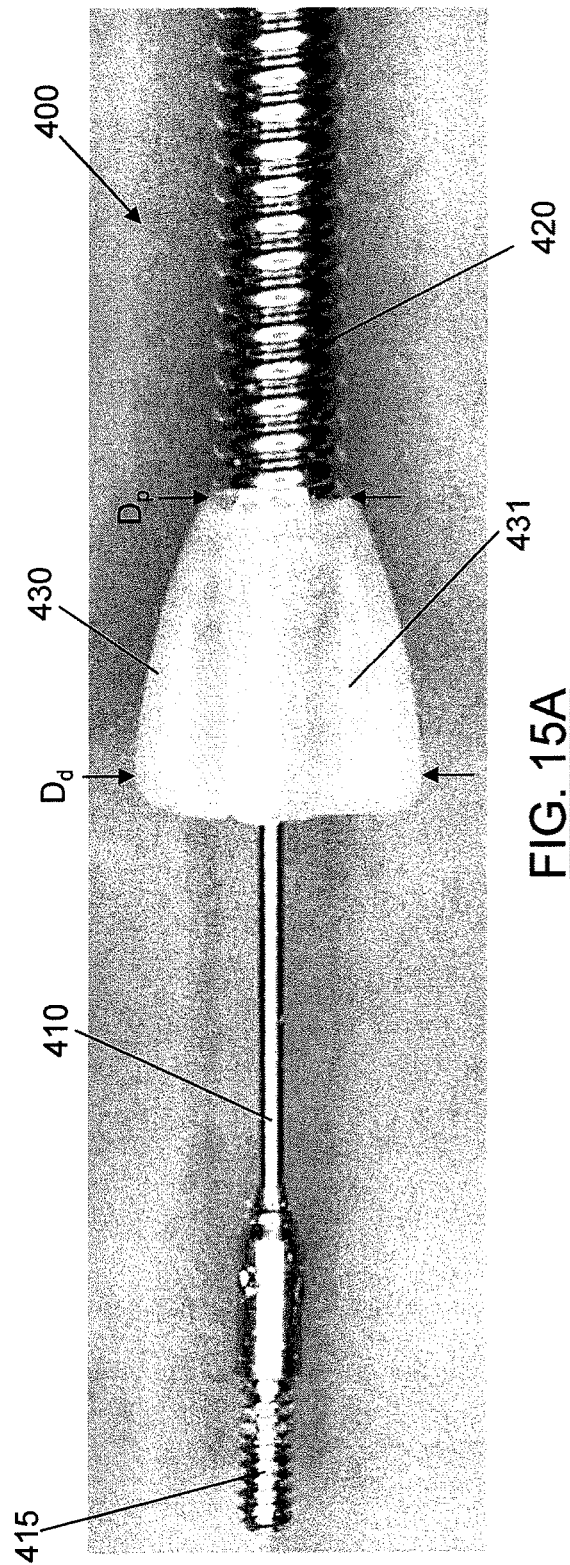
FIG. 15A is a schematic illustration of a delivery device in a first position according to an exemplary embodiment.
Figure 15B:
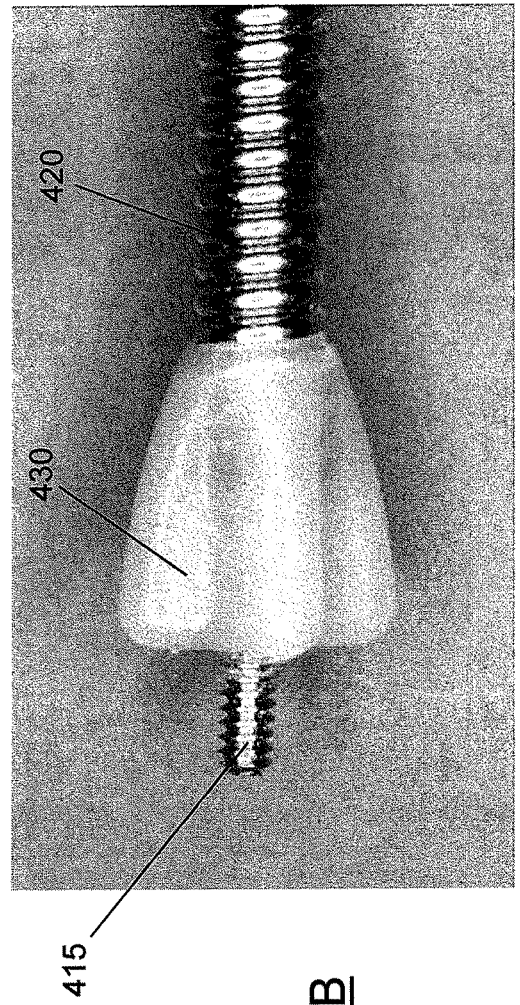
FIG. 15B is a schematic illustration of a delivery device in a second position according to an exemplary embodiment.
Figure 16:
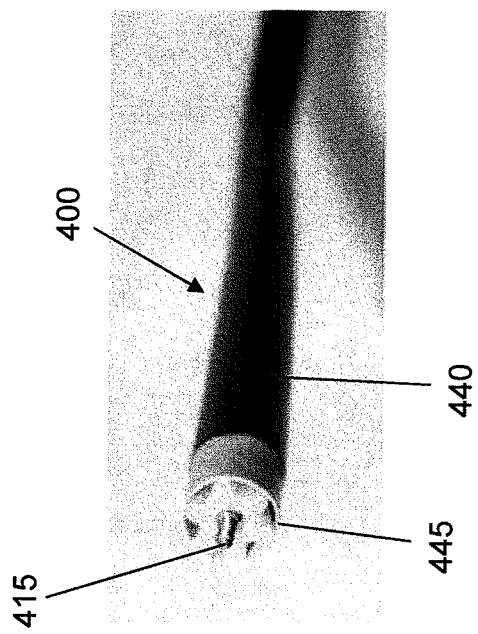
FIG. 16 is a schematic illustration of the delivery device of FIGS. 15A and 15B showing the guide member disposed within the lumen of a delivery catheter.

The method depicted in FIG. 14 and described above represents only one method for making a medical device for placement in a body lumen. Similarly, the method depicted in FIG. 18 and described above represents only one method for delivering a medical device. In some embodiments, certain ones of the steps described above may be modified or further amplified. Furthermore, in some embodiments, additional optional steps may be included, some examples of which are shown in dashed lines in FIGS. 14 and 18. Modifications, additions, or amplifications to the steps above may be performed in any order and in any combination. The particular methods of manufacturing and delivery will depend on the desired configuration of the medical device, the patient's anatomy, the condition and location of the target site, the preferences of the practitioner, and/or other considerations.

This invention has been described herein in considerable detail in order to comply with the Patent Statutes and to provide those skilled in the art with the information needed to apply the novel principles and to construct and use embodiments of the example as required. However, it is to be understood that specifically different devices can carry out the invention and that various modifications can be accomplished without departing from the scope of the invention itself. For example, options shown for one embodiment could easily be applied to other embodiments, as desired for a particular application, without departing from the scope of this invention.

That which is claimed:

1. A method of making a medical device for placement in a body lumen comprising:
    braiding a plurality of strands defining proximal strand ends to form a tubular structure;
    attaching a first end feature defining a proximal end and a distal end to the proximal strand ends via the proximal end of the first end feature; and
    molding the tubular structure to define a first expanded volume portion proximate to the distal end of the first end feature.

2. The method of claim 1, wherein attaching the first end feature to the proximal strand ends comprises at least partially inverting the proximal strand ends at the proximal end of the first end feature.

3. The method of claim 2, wherein attaching the first end feature to the proximal strand ends comprises at least partially inverting the proximal strand ends between an inner bushing and an outer bushing of the first end feature.

4. The method of claim 3 further comprising fusing the inner bushing and the outer bushing to the proximal strand ends.

5. The method of claim 2, wherein inverting the proximal strand ends comprises surrounding a circumferential surface of the first end feature, the circumferential surface extending between the proximal and distal ends of the first end feature.

6. The method of claim 2, wherein inverting the proximal strand ends comprises defining a first transition diameter proximate the expanded volume portion and a second transition diameter proximate the proximal end of the first end feature, wherein the second transition diameter is less than the first transition diameter.

7. The method of claim 1, wherein attaching the first end feature to the proximal ends strands comprises attaching the first end feature proximate to a proximal end of the medical device.

8. The method of claim 1, further comprising:
    braiding the plurality of strands further defining distal end strands; and
    attaching a second end feature defining a proximal end and a distal end to the distal strand ends via the distal end of the second end feature.

9. The method of claim 1, further comprising molding the tubular structure to define a second expanded volume portion distal to the first expanded volume portion, wherein the first expanded volume portion is disc shaped and the second expanded volume portion is cylindrically shaped.

10. The method of claim 9, further comprising molding the tubular structure to define a flexible connecting portion extending between the first expanded volume portion and the second expanded volume portion.

11. The method of claim 10, wherein molding the tubular structure to define the flexible connecting portion comprises molding the tubular structure to define a conical surface of the second expanded volume portion such that the flexible connecting portion is partially recessed within the second expanded volume portion.

12. The method of claim 1, further comprising coupling a plurality of retention hooks to the tubular structure.

13. The method of claim 1, further comprising coating the plurality of strands with a thrombogenic agent.

14. The method of claim 1, further comprising filling the tubular structure with a polymer fabric.

15. A method of making a medical device for placement in a body lumen comprising:
    braiding a plurality of strands defining proximal strand ends to form a tubular structure;
    attaching a first end feature defining a proximal end and a distal end to the proximal strand ends via the proximal end of the first end feature; and
    molding the tubular structure to define a first expanded volume portion proximate to the first end feature, including defining a proximal plane of the first expanded volume portion, wherein the distal end of the proximal end feature is substantially co-planar with the proximal plane of the first expanded volume portion when the medical device is in an expanded configuration.

16. The method of claim 15, wherein attaching the first end feature to the proximal strand ends comprises at least partially inverting the proximal strand ends at the proximal end of the first end feature, wherein the proximal end of the first end feature is proximal to the proximal plane of the first expanded volume portion when the medical device is in the expanded configuration.

17. A method of making a medical device for placement in a body lumen comprising:
    braiding a first plurality of strands defining proximal strand ends to form a first tubular structure;
    attaching a first end feature defining a proximal end and a distal end to the proximal strand ends via the proximal end of the first end feature; and
    braiding a second plurality of strands to form a second tubular structure, such that the medical device includes an inner braided layer defined by one of the first and second tubular structures and an outer braided layer defined by the other of the first and second tubular structures.

* * * * *